(12) United States Patent
Hahn et al.

(10) Patent No.: US 10,852,268 B2
(45) Date of Patent: Dec. 1, 2020

(54) ELECTROCHEMICAL SENSOR INCLUDING MULTIPLE WORK ELECTRODES AND COMMON REFERENCE ELECTRODE

(71) Applicant: Medtronic, Inc., Minneapolis, MN (US)

(72) Inventors: Daniel Hahn, Tustin, CA (US); Mohsen Askarinya, Chandler, AZ (US); James K. Carney, Roseville, MN (US); Patrick W. Kinzie, Glendale, AZ (US); Jennifer Lorenz Marckmann, Tempe, AZ (US); Randal C. Schulhauser, Phoenix, AZ (US); Santhisagar Vaddiraju, Plymouth, MN (US); Akhil Srinivasan, Northridge, CA (US); David Probst, Chandler, AZ (US); Alejo Chavez Gaxiola, Tempe, AZ (US)

(73) Assignee: Medtronic, Inc., Minneapolis, MN (US)

( * ) Notice: Subject to any disclaimer, the term of this patent is extended or adjusted under 35 U.S.C. 154(b) by 220 days.

(21) Appl. No.: 16/116,306

(22) Filed: Aug. 29, 2018

(65) Prior Publication Data

US 2020/0072782 A1 Mar. 5, 2020

(51) Int. Cl.
*G01N 27/327* (2006.01)
*G01N 33/483* (2006.01)

(52) U.S. Cl.
CPC ..... *G01N 27/3272* (2013.01); *G01N 27/3276* (2013.01); *G01N 27/3277* (2013.01); *G01N 33/4836* (2013.01)

(58) Field of Classification Search
CPC .............. G01N 33/4836; G01N 27/327–3272
See application file for complete search history.

(56) References Cited

U.S. PATENT DOCUMENTS

| 4,225,410 A * | 9/1980 | Pace | G01N 33/492 |
| | | | 204/406 |
| 4,454,007 A * | 6/1984 | Pace | G01N 27/3335 |
| | | | 204/403.06 |

(Continued)

FOREIGN PATENT DOCUMENTS

| EP | 0554955 A1 | 8/1993 |
| WO | 1990/05910 A1 | 5/1990 |

(Continued)

OTHER PUBLICATIONS

Metters et al., "Screen-printed back-to-back electroanalytical sensors," Analyst, 2014, 139, 5339 (Year: 2014).*

(Continued)

*Primary Examiner* — Alexander S Noguerola
(74) *Attorney, Agent, or Firm* — Shumaker & Sieffert, P.A.

(57) ABSTRACT

An electrochemical sensor may include a common reference electrode, at least one counter electrode, and a work electrode platform including a plurality of respective work electrodes. Each respective work electrode of the plurality of respective work electrodes may be electrically coupled to the common reference electrode and include a respective reagent substrate configured to react with a respective analyte to produce a signal indicative of a concentration of the respective analyte.

35 Claims, 12 Drawing Sheets

(56) References Cited

U.S. PATENT DOCUMENTS

| | | | | |
|---|---|---|---|---|
| 5,063,081 | A | * | 11/1991 | Cozzette ............... B01L 3/0268 204/403.1 |
| 5,683,562 | A | * | 11/1997 | Schaffar ................. C12Q 1/001 204/282 |
| 6,952,604 | B2 | * | 10/2005 | DeNuzzio .......... A61B 5/14532 600/345 |
| 7,163,511 | B2 | | 1/2007 | Conn et al. |
| 9,554,725 | B2 | | 1/2017 | Katra et al. |
| 2005/0027175 | A1 | | 2/2005 | Yang |
| 2012/0181184 | A1 | * | 7/2012 | Whitesides ........... B01L 3/5027 205/775 |
| 2017/0020415 | A1 | | 1/2017 | Scherer et al. |

FOREIGN PATENT DOCUMENTS

| | | |
|---|---|---|
| WO | 1999/45375 A1 | 9/1999 |
| WO | 2015112638 A1 | 7/2015 |
| WO | 2018/075824 A1 | 4/2018 |

OTHER PUBLICATIONS (PCT/US2019/048268) PCT Notification of Transmittal of the International Search Report and the Written Opinion of the International Searching Authority, dated Jan. Dec. 5, 2019, 13 pages.

(PCT/US2019/048274) PCT Notification of Transmittal of the International Search Report and the Written Opinion of the International Searching Authority, dated Dec. 5, 2019, 12 pages.

"A chip placed under the skin for more precise medicine," Mediacom, accessed from https://actu.epfl.ch/news/a-chip-placed-under-the-skin-for-more-precise-medi/, Apr. 27, 2015, 2 pp.

Baj-Rossi, et al., "Full Fabrication and Packaging of an Implantable Multi-Panel Device for Monitoring of Metabolites in Small Animals," IEEE Transactions on Biomedical Circuits and Systems, vol. 8, No. 5, Oct. 2014, pp. 636-647.

"Under the skin, a tiny laboratory," Mediacom, accessed on https://actu.epfl.ch/news/under-the-skin-a-tiny-laboratory/, Mar. 20, 2013, 2 pp.

U.S. Appl. No. 16/116,346, filed by Daniel Hahn et al., filed Aug. 29, 2018.

* cited by examiner

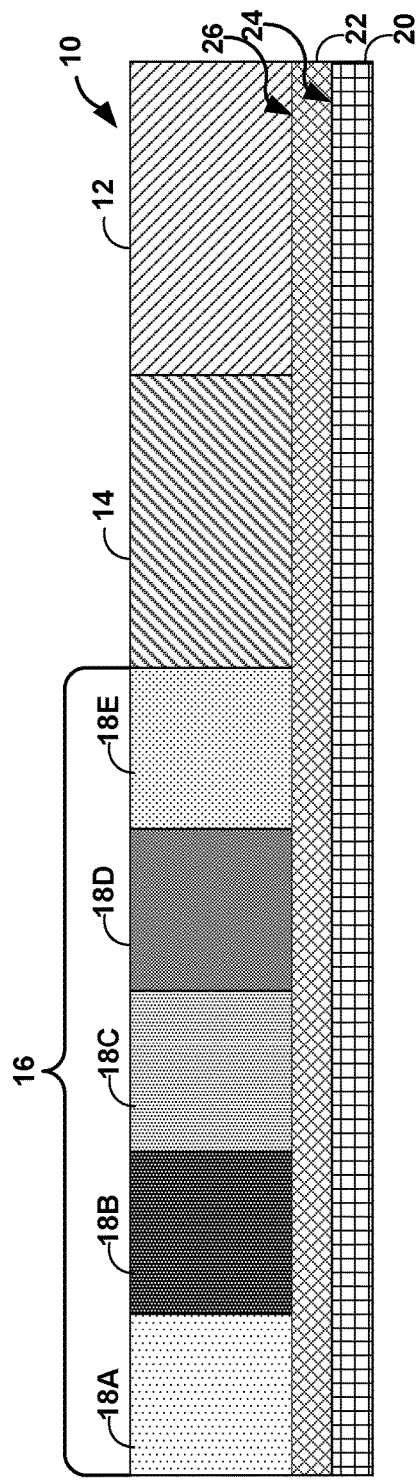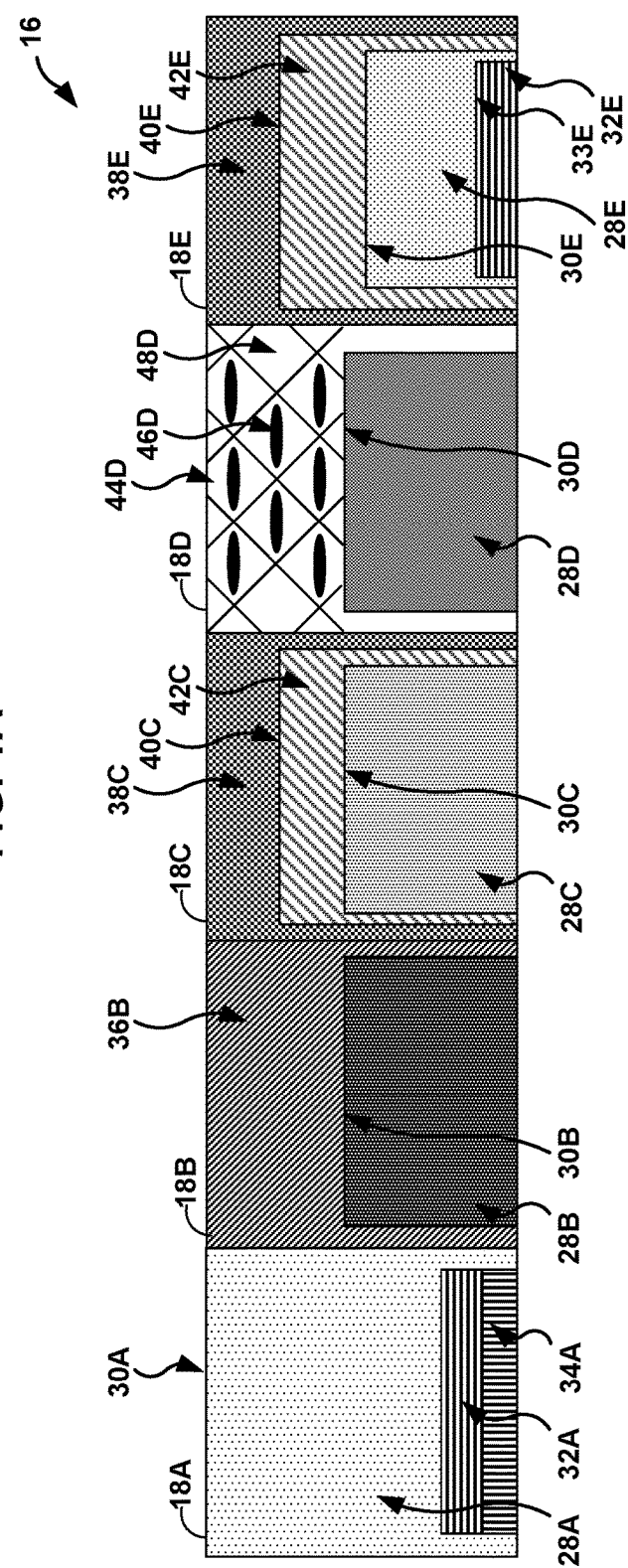
FIG. 1A
FIG. 1B

ELECTROCHEMICAL SENSOR INCLUDING MULTIPLE WORK ELECTRODES AND COMMON REFERENCE ELECTRODE

FIELD

The present technology is related generally to methods and devices for measuring an analyte present in a biological system.

BACKGROUND

Laboratory tests are often used to measure analyte concentrations in fluids, such as fluids in a biological system. For example, a basic metabolic panel (BMP) is a typical lab test that includes three types of serum markers measuring seven analyte concentrations: an electrolyte panel that includes measurement of the concentrations of sodium, chloride, potassium, and bicarbonate/carbon dioxide; a renal function test that includes measurement of the concentration of blood urea nitrogen ("BUN") and creatinine; and a blood glucose test that includes measurement of the concentration of glucose. Other laboratory tests may be used to measure different analytes. A typical BMP, or other lab laboratory test, requires a biological sample, e.g., blood, be taken from a patient and analyzed by bench top and/or clinical equipment to determine analyte concentrations.

SUMMARY

A medical device may include an electrochemical sensor including a common reference electrode, at least one counter electrode, a work electrode platform having a plurality of respective work electrodes, processing circuitry, an antenna, and a power source. The medical device may be insertable into a biological system, such as insertable transcutaneously into the interstitial fluid of a human patient. Each respective work electrode of the plurality of respective work electrodes may produce a respective signal indicative of a concentration of a respective analyte in the biological system. The processing circuitry may retrieve, identify, and process a respective signal from a respective work electrode to determine the concentration of a respective analyte. In this way, the medical device may enable continuous or near continuous monitoring of the multiple analyte concentrations in a biological system. By using a common reference electrode and, optionally, one or more counter electrodes that are shared among two or more respective work electrodes, a size of the medical device may be reduced, reducing the effect of insertion of the medical device in a patient.

In some examples, the disclosure describes an electrochemical sensor that includes a common reference electrode, at least one counter electrode, and a work electrode platform including a plurality of respective work electrodes. Each respective work electrode of the plurality of respective work electrodes may be electrically coupled to the common reference electrode and includes a respective reagent substrate configured to react with a respective analyte to produce a signal indicative of a concentration of the respective analyte.

In some examples, the disclosure describes a biocompatible medical device that includes an electrochemical sensor having a common reference electrode, at least one counter electrode, and a work electrode platform including a plurality of respective work electrodes. Each respective work electrode of the plurality of respective work electrodes may be electrically coupled to the common reference electrode and includes a respective reagent substrate configured to react with a respective analyte to produce a respective signal indicative of a concentration of the respective analyte. The biocompatible medical device also includes processing circuitry operatively coupled to the electrochemical sensor. The processing circuitry may be configured to receive from the electrochemical sensor a plurality of signals from the plurality of respective work electrodes, identify the respective signal corresponding to a respective selected work electrode of the plurality of respective work electrodes, and process the identified signal to determine the concentration of the respective analyte associated with the respective selected work electrode. The biocompatible medical device also includes an antenna operatively coupled to the processing circuitry and a power source operatively coupled to the processing circuitry.

In some examples, the disclosure describes a method of forming an electrochemical sensor, that includes forming a common reference electrode. The method also includes forming at least one counter electrode. The method also includes forming a work electrode platform including a plurality of respective work electrodes on at least a portion of the second major surface. Each respective work electrode of the plurality of respective work electrodes includes a respective reagent substrate configured to react with a respective analyte to produce a signal indicative of a concentration of the respective analyte.

In some examples, the disclosure describes a method of detecting a concentration of an analyte, that includes generating, by an electrochemical sensor of a medical device, a plurality of signals in response to a plurality of analytes. The electrochemical sensor includes a common reference electrode, at least one counter electrode; and a work electrode platform including a plurality of respective work electrodes. Each respective work electrode of the plurality of respective work electrodes may be electrically coupled to the common reference electrode and includes a respective reagent substrate configured to react with a respective analyte to produce a respective signal of the plurality of signals indicative of a concentration of the respective analyte. The method also includes receiving, by processing circuitry of the medical device operatively coupled to the electrochemical sensor, the plurality of signals. The method also includes identifying, by the processing circuitry, the respective signal of the plurality of signals corresponding to a respective selected work electrode of the plurality of respective work electrodes. The method also includes processing, by the processing circuitry, the identified signal to determine the concentration of the respective analyte associated with the respective selected work electrode.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

BRIEF DESCRIPTION OF THE DRAWINGS

FIG. 1A is a schematic and conceptual diagram illustrating a cross-sectional side view of an example electrochemical sensor including a counter electrode, a common reference electrode, and a work platform having a plurality of respective work electrodes.

FIG. 1B is a schematic and conceptual diagram illustrating a cross-sectional side view of an example plurality of respective work electrodes with each respective work electrode of the plurality of respective work electrodes having a selected chemistry.

Figure 2:
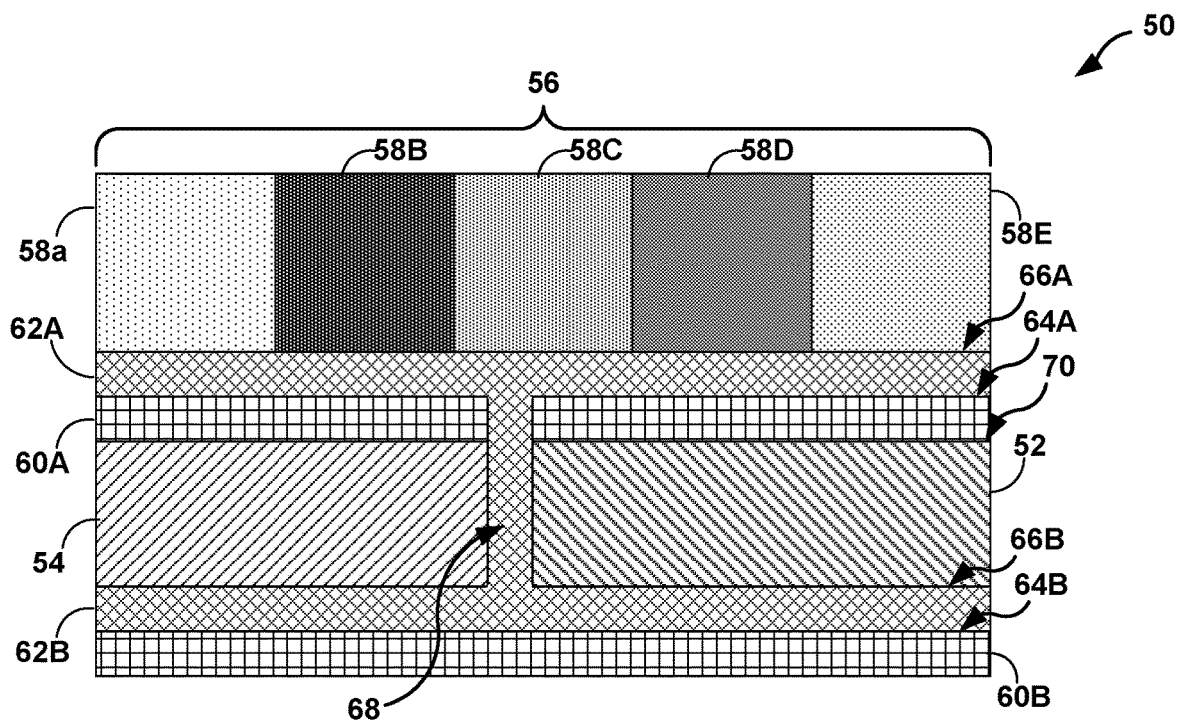
FIG. 2 is a schematic and conceptual diagram illustrating a cross-sectional side view of an example electrochemical sensor including a work platform having a plurality of respective work electrodes stacked on a counter electrode and a common reference electrode.

The details of one or more examples of this disclosure are set forth in the accompanying drawings and the description below. Other features, objects, and advantages of this disclosure will be apparent from the description and drawings, and from the claims.

DETAILED DESCRIPTION

A medical device may include an electrochemical sensor, processing circuitry, an antenna, and a power source. The electrochemical sensor may include a common reference electrode, at least one counter electrode, and a work electrode platform having a plurality of respective work electrodes. In some examples, the common reference electrode and the at least one counter electrode may be operatively coupled to each work electrode of the plurality of respective work electrodes. Using a single, common reference electrode and, in some examples, a single counter electrode may reduce the size of the electrochemical sensor.

Each respective work electrode of the plurality of respective work electrodes may include a respective reagent substrate configured to react with a respective analyte, e.g., an analyte present in a sample fluid to which the plurality of respective work electrodes are exposed. In some examples, a respective membrane disposed on the respective reagent substrate, such as a limiting membrane and/or a selective ion transfer membrane, may be selectively permeable to the respective analyte and used to control the extent or rate of reaction of the analyte at a surface of the reagent substrate, e.g., by controlling a rate of exposure of the reagent substrate to the analyte. In this way, the chemistry of the respective work electrode may be selected to be specific to a respective analyte. In some examples, a reaction of the respective analyte with the respective reagent substrate, e.g., an oxidation reaction or a reduction reaction, may produce, or at least partially cause the generation of, a respective signal indicative of a respective concentration of the respective analyte. In some examples, an interaction of the respective analyte with the respective reagent substrate, e.g., at the double layer, may produce, or at least partially cause the generation of, a respective signal indicative of a respective concentration of the respective analyte. In some examples, the respective signal may include an electrical signal resulting from a change in current, potential, or impedance at the respective work electrode. In this way, the plurality of respective work electrodes may produce respective signals indicative of respective analytes.

The medical device also may include processing circuitry operatively coupled to the electrochemical sensor. The processing circuitry may be configured to receive from the electrochemical sensor the plurality of signals indicative of respective analytes. The processing circuitry may identify a respective signal of the plurality of signals corresponding to a respective selected work electrode of the plurality of respective work electrodes. The processing circuitry may process the identified signal to determine the concentration of the respective analyte associated with the respective selected work electrode. In this way, the processing circuitry may retrieve, identify, and process respective signals of the plurality of signals to determine the respective concentrations of respective analytes.

In some examples, the medical device may be insertable into a biological system, such as interstitial fluid of a human patient. For example, the electrochemical sensor and processing circuitry may include biocompatible materials transcutaneously insertable into the interstitial fluid of a human patient. Each of the processing circuitry, common reference electrode, counter electrode, and work electrode platform may be layered or stacked inside a housing to reduce the size of the medical device. The medical device may include a power source operatively coupled to the processing circuitry to enable the medical device to operate completely within the biological system. The medical device may include an antenna operatively coupled to the processing circuitry to enable the medical device to communicate to an external device, e.g., while operating completely within a biological system. In this way, the medical device may enable continuous monitoring of the multiple analyte concentrations in a biological system.

FIG. 1A is a schematic and conceptual diagram illustrating a cross-sectional side view of an example electrochemical sensor 10 including at least one counter electrode 12, a common reference electrode 14, and a work platform 16 including a plurality of respective work electrodes 18A, 18B, 18C, 18D, and 18E (collectively, "work electrodes 18"). In some examples, electrochemical sensor 10 includes fewer or more electrodes. For example, electrochemical sensor 10 may include only counter electrode 12 and work platform 16, only common reference electrode 14 and work platform 16, more than one counter electrode 12, more than one reference electrode 14, or more than five work electrodes 18, such as seven work electrodes 18, ten work electrodes 18, or more.

In the example illustrated in FIG. 1A, electrochemical sensor 10 includes a dielectric substrate layer 20 defining a first major surface 24. In some examples, dielectric substrate layer 20 may include a biocompatible polymer, such as polyamide or polyimide, liquid crystal polymer, silica glass, such as a glass wafer, sapphire, such as a sapphire wafer, or silicon. In some examples, first major surface 24 is substantially planar. In other examples, first major surface 24 may include surface features, such as ridges, valleys, or apertures, corresponding to features such as electrical traces or through vias. Surface features on or in first major surface 24 may be formed by any suitable means, such as, for example, machining, laser etching, chemical etching, or semiconductor manufacturing techniques such as front-end-of-line (FEOL) processes. In this way, dielectric substrate layer 20 may be formed to support additional layers, facilitate manufacture of the electrochemical sensor 10, or both.

An interconnect layer 22 is on first major surface 24 of dielectric layer 20. Interconnect layer 22 includes an electrically conductive material, such as, for example, aluminum, cadmium, chromium, copper, gold, nickel, platinum, titanium, indium nitride, indium phosphide, zinc oxide, alloys thereof, or the like. In some examples, first major surface 24 may be metallized by, for example, chemical vapor deposition, physical vapor deposition, thermal spraying, cold spraying, or the like, to form interconnect layer 22. Interconnect layer 22 defines a second major surface 26 opposite first major surface 24. Counter electrode 12, common reference electrode 14, and work platform 16 may be disposed on second major surface 26 to electrically couple each respective work electrode of work electrodes 18 to one or both of counter electrode 12 and common reference electrode 14. In some examples, interconnect layer 22 may be operatively coupled to a computing device, such as processing circuitry, to facilitate transmission of a signal from a respective work electrode of work electrodes 18 to the computing device. In some examples, interconnect layer 22 may form a plurality of electrical traces, e.g., formed using semiconductor manufacturing techniques such as back-end-of-line (BEOL) processes. A respective electrical trace or the plurality of electrical traces may electrically couple a respective work electrode of work electrodes 18 to one or more of a computing device, counter electrode 12, or common reference electrode 14.

Electrochemical sensor 10 is configured to detect the concentration of each of a plurality of analytes present in a sample fluid. In some examples, the sample fluid may include a biological fluid, such as blood, interstitial fluid, saliva, urine, spinal fluid, peritoneal fluid, or the like. In some examples, the plurality of analytes include, but are not limited to, one or more of sodium, chloride, potassium, bicarbonate/carbon dioxide, blood urea nitrogen ("BUN"), creatinine, glucose, brain natriuretic peptide (BNP), C-reactive protein (CRP), troponin I (cTnI), lactate, pH, L-dopa, and the like. Each respective work electrode of work electrodes 18 and, in some examples, counter electrode 12 and/or common reference electrode 14, may be fluidly coupled to the sample fluid. In this way, electrochemical sensor 10 may enable continuous or near continuous monitoring of the multiple analyte concentrations in the sample fluid. By using a common reference electrode and, optionally, one or more counter electrodes that are shared among two or more respective work electrodes, a size of electrochemical sensor 10 may be reduced.

Counter electrode 12 (e.g., auxiliary cell) may be disposed on interconnect layer 22. Counter electrode 12 may be configured to function as a cathode when a respective work electrode of work electrodes 18 is operating as an anode or vice versa. In some examples, counter electrode 12 may include an electrochemically inert material, such as copper, gold, indium tin oxide, platinum, silver, silver/silver chloride, titanium, tungsten, tantalum, alloys thereof, carbon, or conductive nanoparticles embedded within a polymeric material. Counter electrode 12 may include any suitable shape, such as rectilinear or curvilinear. In some examples, counter electrode 12 may define a rectangular shape. In some examples, a length of counter electrode 12 is between approximately 0.2 millimeters and approximately 1 centimeter, such as approximately 8.5 millimeters. In some examples, a width of counter electrode 12 is between approximately 0.2 millimeters and approximately 1 centimeter, such as approximately 8.5 millimeters. In some examples, counter electrode 12 may include a surface area larger than each respective work electrode of work electrodes 18. For example, counter electrode 12 may include a surface area that is approximately two to one hundred times the surface area of each respective work electrode of work electrodes 18. In some examples, the larger surface area of counter electrode 12 relative to work electrodes 18 may ensure that a half-reaction occurring at counter electrode 12 may occur fast enough so as not to limit the reactions at work electrodes 18.

In some examples, counter electrode 12 and a respective work electrode of work electrodes 18 may be configured to form a circuit over which current is either applied or measured. The potential of counter electrode 12 may be adjusted to balance a respective reaction occurring at a respective work electrode of work electrodes 18. In this way, the potential of the respective work electrode of work electrodes 18 may be measured against common reference electrode 14 without passing current over common reference electrode 14, which may compromise the stability of common reference electrode 14. In some examples, counter electrode 12 may be separated from work electrodes 18 by, for example, a dielectric barrier and/or orientation of work electrodes 18 with respect to counter electrode 12, to reduce byproducts generated at counter electrode 12 from contaminating the sample fluid. For example, if a reduction reaction is being performed at a respective work electrode of work electrodes 18, oxygen may be evolved from counter electrode 12.

Common reference electrode 14 may be configured to provide a stable and known electrode potential. In some examples, common reference electrode 14 may provide a stable potential by using a redox based system. For example, common reference electrode 14 may include a silver/silver chloride electrode having a potential of about 0.197 volts. Common reference electrode 14 including other materials may have a different stable and known electrode potential. In some examples, common reference electrode 14 may include gold, platinum, silver/silver chloride, hydrogen electrode, copper sulfate, or palladium. Common reference electrode 14 may include any suitable shape, such as rectilinear or curvilinear. In some examples, common reference electrode 14 may define a rectangular shape. In some examples, a length of common reference electrode 14 is between approximately 0.2 millimeters and approximately 1 centimeter, such as approximately 8.5 millimeters. In some examples, a width of common reference electrode 14 is between approximately 0.2 millimeters and approximately 1 centimeter, such as approximately 8.5 millimeters. In some examples, electrochemical sensor 10 may use an external driving voltage. In examples in which a driving voltage is applied to a respective work electrode of work electrodes 18, common reference electrode 14 may stabilize the driving voltage at the respective work electrode of work electrodes 18.

Each respective work electrode of work electrodes 18 may include a selected chemistry. For example, each respective work electrode of work electrodes 18 includes a respective reagent substrate disposed on second major surface 26. In some examples, a reaction of a respective analyte with a corresponding respective reagent substrate may cause electron transfer between a respective work electrode of work electrodes 18 and interconnect layer 22 (e.g., producing a current). In some examples, a reaction of a respective analyte with a corresponding respective reagent substrate may contribute to the potential in a respective work electrode of work electrodes 18 (e.g., producing a voltage). In some examples, interaction of a respective analyte with a corresponding respective reagent substrate may contribute to the resistivity of a respective work electrode of work electrodes 18 (e.g., changing an impedance of the respective work electrode of work electrodes 18 at the double layer). In this way, electrochemical sensor 10 may produce a current, a potential, or an impedance that may be processed by, for example, processing circuitry operatively coupled to each respective work electrode of work electrodes 18, and which allows detection of an analyte.

Each respective work electrode of work electrodes 18 may include any suitable shape, such as rectilinear or curvilinear. In some examples, each work electrode of work electrodes 18 may define a rectangular shape. In some examples, a length of each respective work electrode of work electrodes 18 is between approximately 0.1 millimeters and approximately 2.5 millimeters, such as approximately 0.5 millimeters. In some examples, a width of each respective work electrode of work electrodes 18 is between approximately 0.1 millimeters and approximately 2.5 millimeter, such as approximately 0.5 millimeters.

Each respective work electrode of work electrodes 18 may one or more layers of materials to enable the respective work electrode of work electrodes 18 to produce a signal in response to the presence of a respective selected analyte. FIG. 1B is a schematic and conceptual diagram illustrating a cross-sectional side view of an example plurality of respective work electrodes 18 with each respective work electrode of the plurality of respective work electrodes 18 having a selected chemistry. As illustrated in FIG. 1B, each respective work electrode of work electrodes 18 may include a respective reagent substrate 28A, 28B, 28C, 28D, and 28E (collectively, "reagent substrates 28") configured to react with a respective analyte or a derivative thereof. For example, work electrode 18A may include reagent substrate 28A. In some examples, a respective analyte may interact with a surface 30A of a respective reagent substrate 28A. For example, the respective analyte may transfer electrons to surface 30A or remove electrons from surface 30A. In some examples, a respective work electrode of work electrodes 18 may include one or more conductive material layers. For example, work electrode 18A may include a first conductive layer 32A and a second conductive layer 34A. Example conductive material layers include, but are not limited to, gold, indium tin oxide, carbon, carbon paste, mesoporous carbon, carbon walled, platinum, shiny platinum, black platinum, polyimide silver, and silver/silver-chloride. In some examples, first conductive layer 32A may include a silver/silver-chloride material. In some examples, second conductive layer 34A may define a surface on which first conductive layer 32A may be disposed. First and second conductive material layers 32A and 34A may facilitate the transfer of electrons to or from interconnect layer 22.

In some examples, a respective reagent substrate of reagent substrates 28 includes a respective immobilization substrate configured to immobilize a respective reagent. In some examples, a respective reagent may include at least one enzyme, such as an oxidase enzyme. In some examples, a respective reagent may be immobilized on an immobilization substrate by, for example, physical entrapment (e.g., a respective reagent physically unable to pass through pores of the immobilization substrate), chemical bonding (e.g., ionic bonding, covalent bonding, van der Waals forces, and the like), or combinations thereof. In some examples, the immobilization substrate may include a polymer, such as polylysine, aminosilane, epoxysilane, or nitrocellulose, or a substrate having a three-dimensional lattice structure, such as a hydrogel, an organogel, or a xerogel. In some examples, the immobilization substrate may include a ligand configured to chemically bond to at least a portion of a respective reagent. For example, a respective immobilization substrate including glutaraldehyde may immobilize glucose oxidase. A respective immobilization substrate including primary amine conjugation enniatin may immobilize (used for sodium Na+ detection) can be immobilized to the working electrode through. In some examples, the immobilization substrate may include, but is not limited to, glutaraldehyde, thiol based conjugation compounds (e.g., 16-mercaptohexadecanoic acid (MHDA), diethyldithiocarbamic acid (DSH), dithiobissuccinimidylundecanoate (DSU), purine conjugation compounds, streptavidin-biotin conjugation compounds, a primary amine and a vinyl pyridine polymer, lysine, 1-ethyl-3-(3-dimethylaminopropyl)carbodiimide hydrochloride (EDC) and N-hydroxysuccinimide (NHS) coupling, agarose based gel and polymer mixtures, silane crosslinker, (hydroxyethyl)methacrylate, and poly(ethylene glycol) diacrylate polymer. By immobilizing a respective reagent, the immobilization substrate may reduce loss of the respective reagent to the sample fluid.

In examples in which a respective reagent substrate of reagent substrates 28 includes at least one enzyme, the at least one enzyme may be selected based on the analyte to be detected with the respective work electrode of work electrodes 18. For example, the at least one enzyme may be selected from the group consisting of glucose oxidase (for detecting glucose), creatinine amidohydrolase (for detecting creatinine), creatine amidinohydrolase (for detecting creatine), sarcosine oxidase (for detecting sarcosine), carbonic anhydrase (for detecting bicarbonate and/or carbon dioxide), choline oxidase (for detecting choline), horseradish peroxidase (for detecting peroxide, oxygen, nitric oxide, biogenic amines, or the like), thiamine oxidase (for detecting thiamine), urease (for detecting urea), glycerol-3-phosphate oxidase (for detecting glycerol-3-phosphate), L-amino acid oxidase (for detecting L-amino acid, such as, e.g., L-alanine), lactate oxidase (for detecting lactate and/or lactic acid), catalase (for detecting hydrogen peroxide, e.g., produced by other enzymatic reactions), alkaline phosphatase (for detecting phosphate esters), alcohol oxidase (for detecting primary alcohols), D-amino acid oxidase (for detecting D-amino acids, such as, e.g., D-serine), cholesterol oxidase (for detecting cholesterol), pyridoxal oxidase (for detecting pyridoxal), NAD(P)H oxidase (for detecting NAD(P)H), and pyruvate oxidase (for detecting pyruvate), or mixtures thereof. In some examples, the at least one enzyme may be selected to react with a selected analyte and provide a reaction pathway to enable detection of the concentration of the selected analyte.

In examples in which a respective reagent substrate of reagent substrates 28 includes glucose oxidase (e.g., notatin), glucose oxidase may oxidize glucose in the sample fluid to produce D-glucono-δ-lactone and hydrogen peroxide. The liberated hydrogen peroxide may be oxidized at, e.g., second major surface 26 or first conductive material layer 32A, to produce an electric current that is proportional to the glucose concentration in the sample fluid.

In examples in which a respective reagent substrate of reagent substrates 28 includes creatinine amidohydrolase, creatinine amidohydrolase may hydrolyze creatinine in the sample fluid to produce creatine. The respective reagent substrate of reagent substrates 28 may also include creatine amidinohydrolase to hydrolyze creatine to form sarconsine. The respective reagent substrate of reagent substrates 28 may also include sarconsine oxidase to oxidize sarconsine to form hydrogen peroxide. The liberated hydrogen peroxide may be oxidized at, e.g., second major surface 26 or first conductive material layer 32A, to produce an electric current that is proportional to the creatinine concentration in the sample fluid.

In examples in which a respective reagent of reagent substrates 28 includes carbonic anhydrase, carbonic anhydrase may be coupled with p-benzoquinone to reduce dissolved carbon dioxide in the sample fluid to produce carbonic acid. The reduction reaction may produce an electric current that is proportional the bicarbonate concentration in the sample fluid.

In examples in which a respective reagent substrate of reagent substrates 28 includes urease, urease may hydrolyze urea to produce ammonium ions. The ammonium ions may produce a potential in a respective work electrode that is associated with the urea concentration, e.g., by the Nernst equation.

In some examples, a respective work electrode of work electrodes 18 may include one or more respective membranes. The one or more membranes may be permeable to a respective analyte and, in some examples, configured to block interfering cellular bodies or molecules from binding or adhering to a respective work electrode of work electrodes 18. For example, a glucose membrane may block large molecules, such as red blood cells, white blood cells, acetaminophen, ascorbic acid, and the like. The one or more membranes may include, for example, one or more limiting membranes, one or more selective ion transfer membranes, one or more ionophore membranes, or combinations thereof. For example, as illustrated in FIG. 1B, work electrode 18B may include reagent substrate 28B defining surface 30B and limiting membrane 36B disposed on surface 30B. Limiting membrane 36B may have a desired permeability to a selected molecule or ion, or group of selected molecules or ions. For example, limiting membrane 36B may reduce migration of a selected molecule or ion, or group of selected molecules or ions, to surface 30B of reagent substrate 28B. Limiting membranes may include, but are not limited to, polyurethane polyurea block copolymer including a mixture of materials, such as, e.g., hexamethylene, diisocyanate, aminopropyl-terminated siloxane polymer, and polyethylene glycol, or a vinyl pyridine-styrene copolymer mixed with epoxy groups and coated with polyethylene glycol. By limiting the amount of a respective analyte reacting with reagent substrate 28B, limiting membrane 36B may reduce limiting the respective reaction due to the amount and/or availability of the respective reagent substrate.

As illustrated in FIG. 1B, work electrode 18C may include reagent substrate 28C defining surface 30C, selective ion transfer membrane 42C disposed on surface 30C and defining surface 40C, and limiting membrane 38C disposed on surface 40C. In other examples, work electrode may not include limiting membrane 38C or may include limiting membrane 38C disposed on surface 30C and defining surface 40C, and selective ion transfer membrane 42C disposed on surface 40C. Selective ion transfer membrane 42C may be selectively permeable to a selected ion or group of ions. For example, selective ion transfer membrane 42C may include a porous material having a net positive (or negative) charge to enabling permeation of ions having a like charge through selective ion transfer membrane 42C, while reducing permeation of ion having an opposite charge. In some examples, selective ion transfer membrane 42C may include, but is not limited to, amino methylated polystyrene salicylaldehyde, dibenzo-18-crown-6, cezomycin, enniatin, gramicidin A, lasalocid, macrolides, monensin, narasin, nigericin, nigericin sodium salt, nonactin, polyimide/lycra blend, salinomycin, valinomycin, or mixtures thereof. In some examples, selective ion transfer membrane 42C may include ion transfer membranes grouped by structural subunits, such as ketone family, ester family, aldehyde family, molecular imprinted polymers (MIP), and the like. By reducing permeability to undesired ions, selective ion transfer membrane 42C may reduce undesired reactions at reagent substrate 28C that may reduce accuracy of the detection of the selected analyte.

In some examples, a selective ion transfer membrane may include an ionophore membrane. For example, as illustrated in FIG. 1B, work electrode 18D may include reagent substrate 28D defining surface 30C and ionophore membrane 44D. In some examples, ionophore membrane 44D may include a plurality of ionophores 46D dispersed in an ionophore matrix material 48D. Plurality of ionophores 46D may be selected to be preferentially permeable to a selected ion or group of ions. In some examples, plurality of ionophores 46D may include, but is not limited to, crown ethers, cryptands, calixarenesm, phenols, amino methylated polystyrene salicylaldehyde, beauvericin, calcimycine, cezomycin, carbonyl cyanide m-chlorophenyl hydrazone, dibenzo-18-crown-6, enniatin, gramicidin A, ionomycin, lasalocid, macrolides, monensin, nigericin, nigericin sodium salt, narasin, nonactin, polyimide/lycra blend, salinomycin, tetronasin, valinomycin, potassium ionophore III (BME 44) or mixtures thereof. Ionophore matrix material 48D may include, but it not limited to, polyvinylchloride, silicone, fluorosilicone, polyurethane, glutaraldehyde, UV curable polymers like PVA-SbQ, PVA hydrogels, pHEMA-HAA crosslinking, and agarose gel.

Each respective work electrode of work electrodes 18 may include any number or arrangement of layers discussed above. For example, as illustrated in FIG. 1B, work electrode 18E may include conductive material layer 32E defining surface 33C, reagent substrate 28E disposed on surface 33E and defining surface 30E, selective ion transfer membrane 42E disposed on surface 30E and defining surface 40E, and limiting membrane 38E disposed on surface 40E. In this way, each respective work electrode of work electrodes 18 may be configured to react with a selected analyte or a derivative thereof to produce a response signal to the presence of the selected analyte.

Various signal processing techniques may be used to detect analytes or concentrations of analytes. For example, one or more of amperometry, potentiometry, and/or electrochemical impedance spectroscopy (EIS) may be used to analyze signals from work electrodes 18. In some examples, a plurality of signal processing techniques may be used to detect a respective analyte or a respective concentration of a respective analyte. For example, two or more respective work electrodes of work electrodes 18 may be configured to detect a respective analyte, where each of the two or more respective work electrodes of work electrode 18 use different signal processing techniques.

One example signal processing technique may include amperometry. Amperometry may be used to measure the reduction or oxidation of a respective analyte at a respective work electrode of work electrodes 18. In examples using amperometry, a working potential applied between a respective work electrode of work electrodes 18 and common reference electrode 14 may generate a current that is carried between the respective work electrode of work electrode 18 and common reference electrode 14. The current may be measured using, for example, an ammeter, a current to frequency converter, or a current to voltage converter, such as a resistor in the current path or a transimpedance amplifier. The current may change as a respective analyte is oxidized or reduced at the respective work electrode of work electrodes 18 (e.g., as electrons are produced by an oxidation reaction or consumed a reduction reaction). For example, the current may be related to the rate of reaction ($V_A$) by the expression $i=nFAV_A$, wherein n is the number of electrons per mole (or the number of electrons per molecule), F is Faraday's constant, and A is the surface area of the respective work electrode. The number of electrons transferred to the respective work electrode, n, may be proportional to the concentration of the analyte in the sample fluid. In this way, the measured current may be associated with the concentration of the analyte in the sample fluid.

In some examples, the applied potential may be adjusted to maximize the response for the analyte of interest while minimizing the response for interfering analytes. For example, a respective analyte may have a higher affinity for a selected working potential or range of working potentials. In some examples, the working potential may be pulsed (e.g., a duration of about one hundred to about nine hundred milliseconds). The pulsed working potential may be followed by a higher potential or a lower potential to at least partially clean the respective analyte from the respective work electrode of work electrodes 18 (e.g., reduce the affinity of the respective analyte for the respective work electrode). In examples in which the working potential is pulsed, the current may be measured only while the working potential is applied.

Potentiometry may be used to measure the potential between two electrodes in a sample fluid. In examples using potentiometry, common reference electrode 14 may have a constant potential irrespective of the concentration of analytes in the sample fluid. A respective work electrode of work electrodes 18 may demonstrate Nernstian response to the composition of the sample fluid. That is, a difference of potential between common reference electrode 14 and the respective work electrode of work electrodes 18 may be proportional to the concentration of the analyte in the sample fluid, e.g., the difference of potential may increase approximately 59 mV for every order of magnitude increase in the concentration of the analyst in the sample fluid. In some examples, a respective work electrode of work electrodes 18 may include an selective ion transport membrane. For example, the selective ion transport membrane may include an ionophore to control transport of a respective analyte to the respective work electrode of work electrodes 18. In some examples, the ionophore may control the transport of, for example, hydrogen ions ($H^+$), sodium ions ($Na^+$), potassium ions ($K^{+'}$), chloride ions ($Cl^-$), calcium ions ($Ca^{2+}$), bicarbonate ($HCO_3^-$), and/or BUN. In this way, a respective work electrode of work electrodes 18 may convert the activity of a respective analyte in the sample fluid into an electrical potential.

The electrical potential may be measured by, for example, a voltmeter, such as a high output impedance amplifier. The measured voltage may be proportional to the ionic activity of the respective analyte according to the Nernst equation. For example, the Nernst equation relates the reduction potential of an electrochemical reaction (half-cell or full cell reaction) to the standard electrode potential, temperature, and activities (often approximated by concentrations) of the chemical species undergoing reduction and oxidation. In one example, the Nernst equation may be given by $E_{cell}=E°+2.3026(RT/zF)\log_{10}(Q_r)$, where $E_{cell}$ is the cell potential (electromotive force, emf) at the temperature of interest, $E°$ is the standard cell potential (millivolts), R is the universal gas constant (Joules per kelvin-mole), T is the temperature (kelvin), z is the number of electrons transferred to the respective work electrode of work electrodes 18, F is Faraday's constant (coulombs per mole of electrons), and $Q_r$ is the reaction quotient of the cell reaction. The number of electrons transferred to the respective work electrode, z, may be proportional to the concentration of the analyte in the sample fluid. In this way, the measured potential may be associated with the concentration of the analyte in the sample fluid.

Electrochemical impedance spectrometry (EIS) is a perturbative characterization of the dynamics of an electrochemical process by determining an impedance of a respective work electrode of work electrodes 18 in a sample fluid (e.g., the electrochemical system) in response to a potential applied to the respective work electrode of work electrodes 18. A current frequency dependence of the impedance of the respective work electrode of work electrodes 18 may be associated with the concentration of a respective analyte in the sample fluid. For example, the limiting membrane of a respective work electrode of work electrodes 18 may be selected to enable approximately steady state diffusion of a target analyte to and from the respective work electrode. A working potential may be applied to the respective work electrode of work electrodes 18, where the working potential may include a direct current polarization potential and a superimposed alternating current potential having a selected frequency (e.g., an excitation signal). The current response (e.g. response signal) may be measured by, for example, an ammeter. The selected frequency may include a frequency predetermined to result in a response signal for a selected analyte (e.g., an optimal frequency for the selected analyte). Additionally, or alternatively, the selected frequency may include a plurality of frequencies applied sequentially, such as, for example, ranging from 1 Hz to 100 kHz (e.g., a frequency sweep). In some examples, the working potential may be selected to the dynamic noise for EIS. In examples in which the excitation signal is sufficiently small, e.g., between approximately 1 millivolts (mV) to 10 mV, the current response may be modeled as a linear electrochemical system.

When modeled as a linear electrochemical system, the impedance with respect to radial frequency, $Z(\omega)$, may be represented as a complex number (based on Euler's relationship $\exp(j\varphi)=\cos(\varphi)-j\sin(\varphi)$) as $Z(\omega)=Z_o(\cos(\varphi)-j\sin(\varphi))$, where $Z_o$ is associated with the working potential, and φ is the phase shift of the response signal. In some examples, the impedance $Z(\omega)$ may be used to produce a Nyquist plot (e.g., real part of the expression for $Z(\omega)$ plotted on the X-axis and the imaginary part of the expression for $Z(\omega)$ is plotted on the Y-axis). In some examples, the impedance $Z(\omega)$ may be used to produce a Bode Plot (e.g., log frequency on the X-axis and both the absolute values of the impedance ($|Z|=Z_0$) and the phase-shift on the Y-axis). In some examples, modulus, admittance, and capacitance may be used to represent the current response and/or transformations thereof. In examples in which the electrochemical process is dependent on diffusion of the respective analyte, the impedance may have a low-frequency character, which may be modeled as a Warburg impedance element. In some examples, an equivalent circuit model, e.g., a Randles circuit model, may be used to process the measure current response to determine the impedance the electrochemical system. In some examples, the double layer of the electrochemical system may be modeled as an imperfect parallel plate capacitor (or a constant phase element), such that the concentration of the analyte may be associated with the determined impedance. In this way, the EIS may be used to determine a concentration of the analyte in the sample fluid. By using EIS to determine impedance of the electrochemical system, the respective analyte may be directly measured in the sample fluid (e.g., EIS may be label free), the excitation frequency may be selected to target a respective analyte, the analyte may not be consumed by a reaction, noise may be measured simultaneously to the response signal to improve the signal-to-noise ratio and evaluate the function of the sensor, and power consumption is reduces compared to other detection methods.

By using a common reference electrode 14 and, optionally, at least one counter electrode 12 that are shared among two or more respective work electrodes 18, a size of electrochemical sensor 10 may be reduced. Reducing the size of electrochemical sensor 10 may enable incorporating electrochemical sensor 10 into a medical device that may be inserted in a patient. Inserting the medical device into the patient may enable continuous or near continuous monitoring of the concentration of an analyte in interstitial fluid of the patient. In this way, the patient may remain ambulatory during monitoring of the concentration of an analyte in interstitial fluid of the patient. Additionally, the concentration of an analyte in interstitial fluid of the patient may be monitored with an increased frequency compared to other methods of monitoring the concentration of an analyte. Increasing the frequency of monitoring may improve the quality of analyte concentration data to improve patient care.

In some examples, counter electrode 12, common reference electrode 14, and work platform 16 may be oriented to reduce the surface area of electrochemical sensor 10. FIG. 2 is a schematic and conceptual diagram illustrating a cross-sectional side view of an example electrochemical sensor 50 including a work platform 56 having a plurality of respective work electrodes 58A, 58B, 58C, 58D, and 58E (collectively, "work electrodes 58") stacked on a counter electrode 52 and a common reference electrode 54. Electrochemical sensor 50 may be the same as or substantially similar to electrochemical sensor 10 illustrated in FIGS. 1A and 1B, except for the differences describe herein. For example, electrochemical sensor 50 may be configured to detect the concentration of each of a plurality of analytes present in a sample fluid operatively coupled to (e.g., in fluid communication with) at least each respective work electrode of work electrodes 58. Counter electrode 52 may be configured to functions as a cathode when a respective work electrode of work electrodes 58 is operating as an anode and vice versa. Common reference electrode 54 may be configured to provide a stable and known electrode potential.

As illustrated in FIG. 2, electrochemical sensor 50 includes first dielectric substrate 60A and second dielectric substrates 60B defining respectively first major surface 64A and third major surfaces 64B. First and second dielectric substrates 60A and 60B may be the same or substantially similar to dielectric substrate 20 illustrated in FIG. 1A. Electrochemical sensor also includes first interconnect layer 62A and second interconnect layer 62B disposed on first and third major surfaces 64A and 64B, respectively. First and second interconnect layers 62A and 62B may be the same as or substantially similar to interconnect layer 22 illustrated in FIG. 1, except for the differences describe herein. For example, first and second interconnect layers 62A and 62B may define second major surface 66A and fourth major surface 66B, respectively, opposite first and third major surfaces 64A and 64B. In some examples, work platform 56 is disposed on second major surface 66A. In some examples, counter electrode 52 and common reference electrode 54 are disposed on fourth major surface 66B.

In some examples, first dielectric substrate 60A may be disposed on a fifth major surface 70 defined by counter electrode 52, common reference electrode 54, or both. By stacking work platform 56 on counter electrode 52, common reference electrode 54, or both, electrochemical sensor 50 may have a smaller surface area compared to, for example, an orientation without stacking work platform 56 on counter electrode 52, common reference electrode 54, or both. In some examples, first and second interconnect layers 62A and 62B may be operatively coupled by one or more through vias 68 or one or more electrical traces. By operatively coupling first and second interconnect layers 62A and 62B with one or more through vias 68, work platform 56 may be operatively coupled to counter electrode 52 and/or common reference electrode 54.

Figure 3:
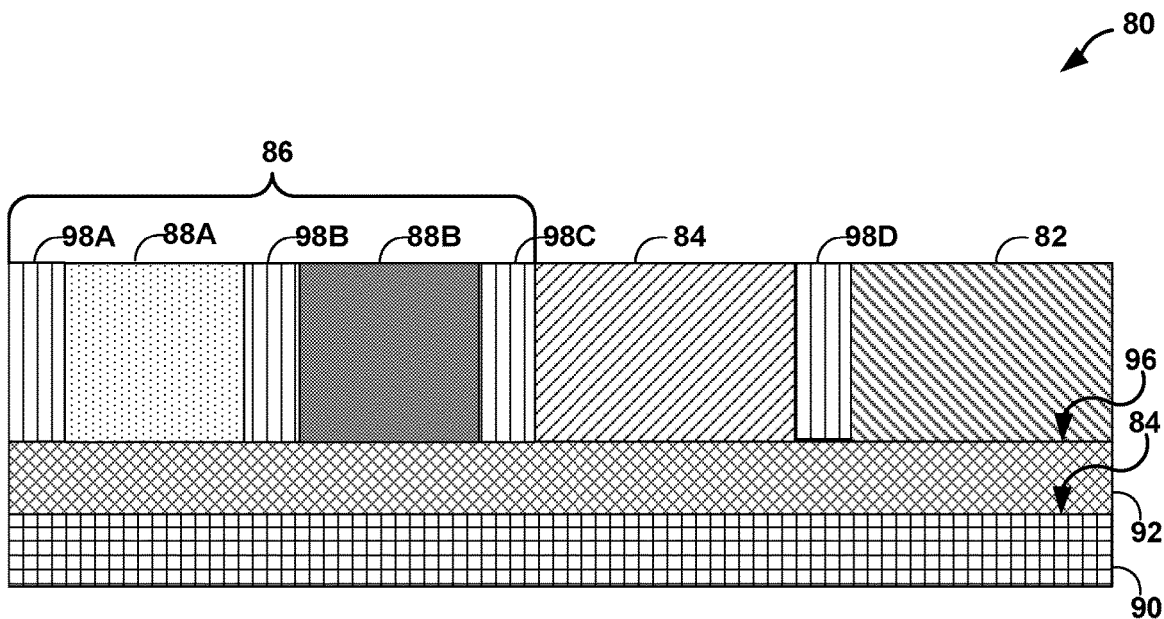
FIG. 3 is a schematic and conceptual diagram illustrating a cross-sectional side view of an example electrochemical sensor including a plurality of dielectric barriers between each pair of adjacent work electrodes of a plurality of respective work electrodes.

In some examples, a dielectric barrier may separate work electrodes, counter electrodes, and common reference electrode to reduce electrical interference, such as electron transfer, between adjacent electrodes. FIG. 3 is a schematic and conceptual diagram illustrating a cross-sectional side view of an example electrochemical sensor 80 including a plurality of dielectric barriers 98A, 98B, 98C and 98D (collectively, "dielectric barriers 98") between each pair of adjacent work electrodes 18. Electrochemical sensor 80 may be the same as or substantially similar to electrochemical sensor 10 illustrated in FIGS. 1A and 1B and electrochemical sensor 50 illustrated in FIG. 2, except for the differences describe herein. For example, electrochemical sensor 80 includes a dielectric substrate layer 90 defining a first major surface 94 and interconnect layer 92 disposed on first major surface 94 and defining second major surface 96. Electrochemical sensor 80 may include a plurality of respective work electrodes 88A and 88B (collectively, "work electrodes 88") disposed on second major surface 96 and configured to detect the concentration of each of a plurality of analytes present in a sample fluid. Electrochemical sensor 80 may include a counter electrode 82 disposed on second major surface 96 and configured to functions as a cathode when a respective work electrode of work electrodes 58 is operating as an anode and vice versa. Electrochemical sensor 60 may also include a common reference electrode 84 disposed on second major surface 96 and configured to provide a stable and known electrode potential.

In some examples, dielectric barriers 98 may be configured to reduce electrical interference between adjacent electrodes. For example, dielectric barriers 98 may reduce electron transfer between adjacent electrodes, reduce electromagnetic interference between adjacent electrode, or both. In some examples, dielectric barriers 98 may include a biocompatible polymer, such as polyamide or polyimide, liquid crystal polymer, silica glass, such as a glass wafer, sapphire, such as a sapphire wafer, or silicon. In some examples, dielectric barriers 98 may be integrally formed with dielectric substrate 90. For example, each respective work electrode of work electrodes 88, counter electrode 82, and common reference electrode 84 may be disposed within a cavity defined by dielectric substrate 90.

Figure 4:
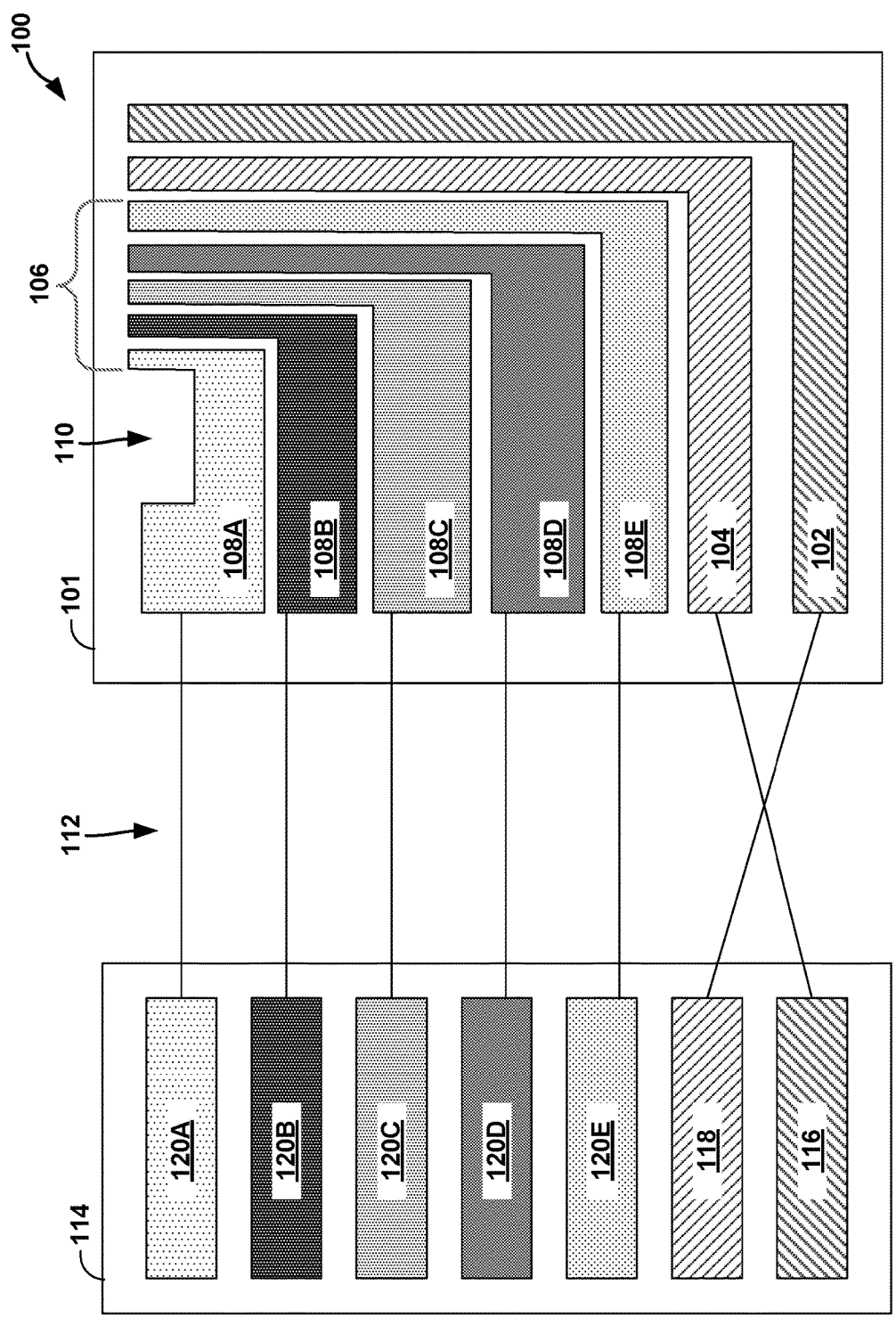
FIG. 4 is a schematic and conceptual diagram illustrating a plan view of an example medical device that includes electrochemical sensor including a counter electrode, a common reference electrode, and a work platform having a plurality of respective work electrodes operatively coupled to corresponding electrical components.

In some examples, component of an electrochemical sensor, including a plurality of work electrodes, at least one counter electrode, and a common reference electrode, may be arranged to facilitate coupling of the electrochemical sensor with a computing device including electronic components, such as processing circuitry. FIG. 4 is a schematic and conceptual diagram illustrating a plan view of an example medical device 100 that includes electrochemical sensor 101 including counter electrode 102, a common reference electrode 104, and a work platform 106 having a plurality of respective work electrodes 108A, 108B, 108C, 108D, and 108E (collectively "work electrodes 108") operatively coupled to corresponding electrical components of electrical components 114. Electrochemical sensor 101 may be the same as or substantially similar to electrochemical sensors 10, 50, and 80 illustrated in FIGS. 1A, 1B, 2, and 3, except for the differences describe herein. For example, electrochemical sensor 110 may be configured to detect the concentration of each of a plurality of analytes present in a sample fluid operatively coupled to (e.g., in fluid communication with) at least each respective work electrode of work electrodes 108. Counter electrode 102 may be configured to functions as a cathode when a respective work electrode of work electrodes 108 is operating as an anode and vice versa. Common reference electrode 104 may be configured to provide a stable and known electrode potential.

Counter electrode 102, common reference electrode 104, and work electrodes 108 may be arranged on dielectric substrate 110 in any suitable orientation. As illustrated in FIG. 4, counter electrode 102, common reference electrode 104, and work electrodes 108 each include a unique size and shape that are arranged in a stacked orientation. By enabling different size, shapes, and/or orientations of counter electrode 102, common reference electrode 104, and work electrodes 108, electrochemical sensor 101 may enable a selected chemistry at each of counter electrode 102, common reference electrode 104, and work electrodes 108.

As discussed above, an interconnect layer may form a plurality of electrical traces, such as, for example, a plurality of interconnects 112. Plurality of interconnects 112 electrically couple at least a portion of counter electrode 102, common reference electrode 104, and work electrodes 108 to a corresponding electrical component of electrical components 114. In some examples, electrical components 114 may include a computing device including processing circuitry. For example, plurality interconnects 112 illustrate an electrical coupling of each of counter electrode 102 to corresponding counter electrode electrical component 118, common reference electrode 104 to corresponding common reference electrode electrical component 116, and respective work electrodes 108A, 108B, 108C, 108D, and 108E to respective corresponding work electrode electrical components 120A, 120B, 120C, 120D, and 120E (collectively, "work electrode electrical components 120").

Figure 5:
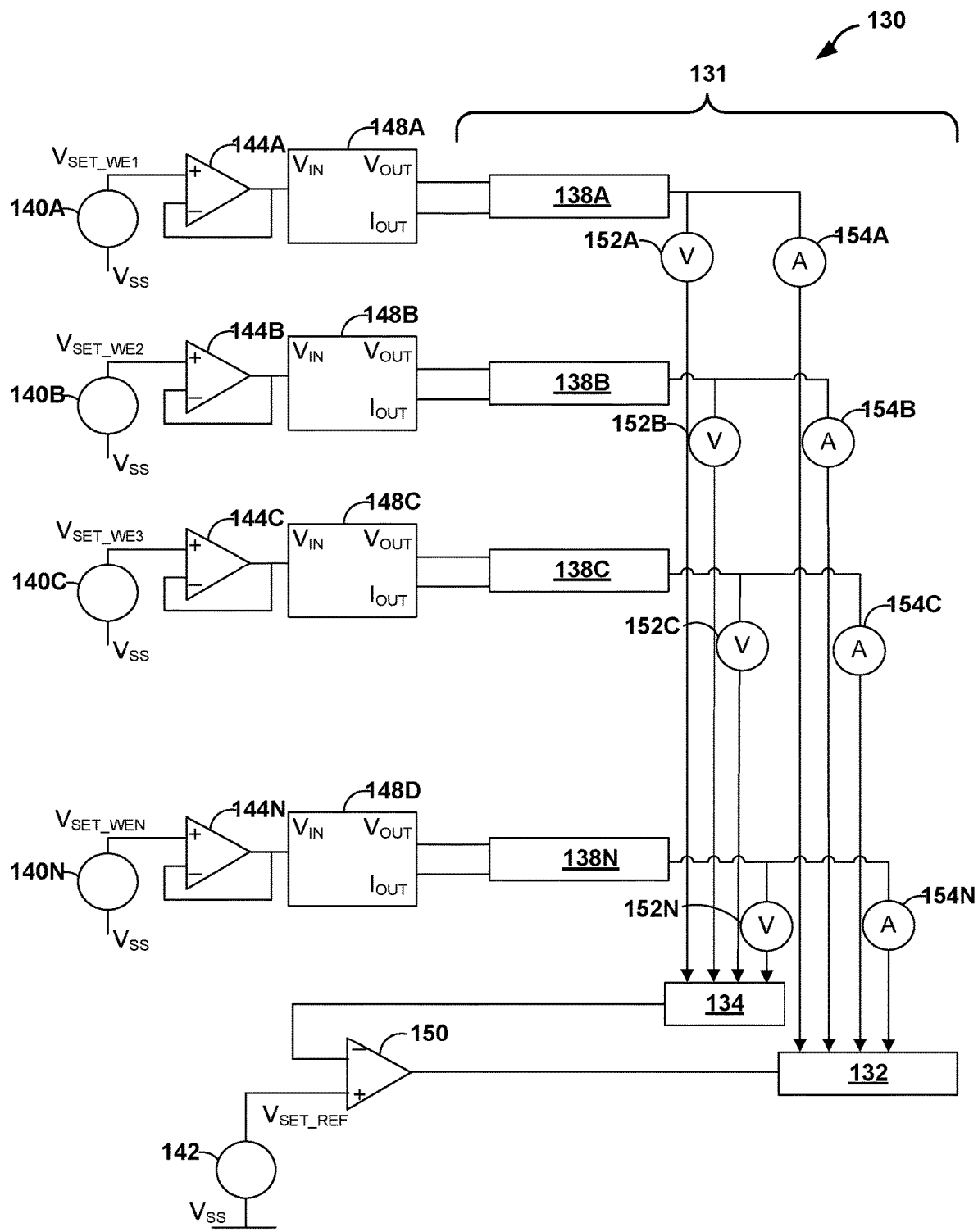
FIG. 5 is a schematic and conceptual partial circuit diagram illustrating an example medical device that includes an electrochemical sensor including a counter electrode, a common reference electrode, and a work platform having a plurality of respective work electrodes operatively coupled to corresponding electrical components.

Counter electrode electrical component 116, common reference electrode electrical component 118, and work electrode electrical components 120 may be configured to enable medical device 100, at least in part, to retrieve, identify, and process respective signals of the plurality of signals (e.g., produced by work electrodes 108) to determine respective concentrations of respective analytes in a sample fluid. For example, each of counter electrode electrical component 118, common reference electrode electrical component 116, and work electrode electrical components 120 may include any suitable electrical component, electrical subcomponent, or combination of electrical components to enable medical device 100, at least in part, to retrieve, identify, and process respective signals of the plurality of signals (e.g., produced by work electrodes 108) to determine respective concentrations of respective analytes in a sample fluid. FIG. 5 is a schematic and conceptual partial circuit diagram illustrating an example medical device 130 including an electrochemical sensor 131 including a counter electrode 132, a common reference electrode 134, and a work platform 136 having a plurality of respective work electrodes 138A, 138B, 138C, and 138N (collectively, "work electrodes 138") operatively coupled to corresponding electrical components. Medical device 130 may be the same as or substantially similar to medical device 100 illustrated in FIG. 4, except for the differences describe herein. For example, medical device 130 may be configured to detect the concentration of each of a plurality of analytes present in a sample fluid operatively coupled to (e.g., in fluid communication with) at least each respective work electrode of work electrodes 138. Counter electrode 132 may be configured to functions as a cathode when a respective work electrode of work electrodes 138 is operating as an anode and vice versa. Common reference electrode 134 may be configured to provide a stable and known electrode potential.

As discussed above, various signal processing techniques include applying a potential and/or current to a respective work electrode of work electrodes 138 and, in some examples, at least one of counter electrode 132 or common reference electrode 134. As illustrated in FIG. 5, medical device 130 may include a respective source supply voltage ($V_{SS}$) 140A, 140B, 140C, and 140N (collectively, "work electrode source supply voltages 140") operatively coupled to each respective work electrode of work electrodes 138. Each respective work electrode source supply voltage 140 may be operatively coupled to an amplifier 144A, 144B, 144C, and 144N (collectively, "amplifiers 144"), which, in some examples, may be non-inverting amplifiers. In some examples, amplifiers 144 may reduce variation in the potential applied to the respective work electrode of work electrodes 138. The output of amplifiers 144 may be input to power electronics 148A, 148B, 148C, and 148N (collectively, "power electronics 148"). A respective power electronics of power electronics 148 may be configured to supply a selected potential, a selected current, or both to a respective work electrode of work electrodes 138. In some examples, power electronics 148 may include a controller to, for example, overlay an AC excitation signal over a DC working potential. In some examples, power electronics 148 may include power conversion circuitry, such as an AC-to-direct-current (AC/DC) conversion device, a DC/DC conversion device, a buck conversion circuit, a boost conversion circuit, a buck-boost conversion circuit, a forward conversion circuit, a resonant-mode conversion circuit, a half-bridge circuit, an H-bridge circuit, and/or any other power conversion circuit. In some examples, power electronics 148 may include one or more switches configured to selectively supply power to a respective work electrode of work electrodes 138. By selecting a respective amplifier of amplifiers 144 and selecting a respective power electronics of power electronics 148, the potential and/or current delivered to a respective working electrode of work electrodes 138 may be controlled, for example, based on a selected signal processing technique for the respective work electrode. Additionally, or alternatively, selectively powering a respective work electrode of work electrodes 138 with one or more switches of power electronics 148 may enable dissipation of gradients, biproducts, or the like resulting from a first work electrode of work electrodes 138 before measuring with a second work electrode of work electrodes to reduce errors in the measurements of the second work electrode.

In some examples, a respective work electrode of work electrodes 138, e.g., an output of a respective work electrode of work electrodes 138, may be operatively coupled to a respective voltmeter of a plurality of voltmeters 152A, 152B, 152C, and 152N (collectively, "voltmeters 152"). In some examples, a respective work electrode of work electrodes 138 may be operatively coupled to a respective ammeter of a plurality of ammeter 154A, 154B, 154C, and 154N (collectively, "ammeter 154"). By operatively coupling work electrodes 138 to voltmeters 152 and ammeters 154, medical device 130 may measure the output potential and current of each respective work electrode of work electrodes 138.

In some examples, work electrodes 138 may be operatively coupled to common reference electrode 134. Common reference electrode 134 may provide a stable and known electrode potential to an inverting input of op amp 150. A source supply voltage ($V_{SS}$) may be operatively coupled to a non-inverting input of op-amp 150. The output of op amp 150 may be operatively coupled to counter electrode 132.

Figure 6:
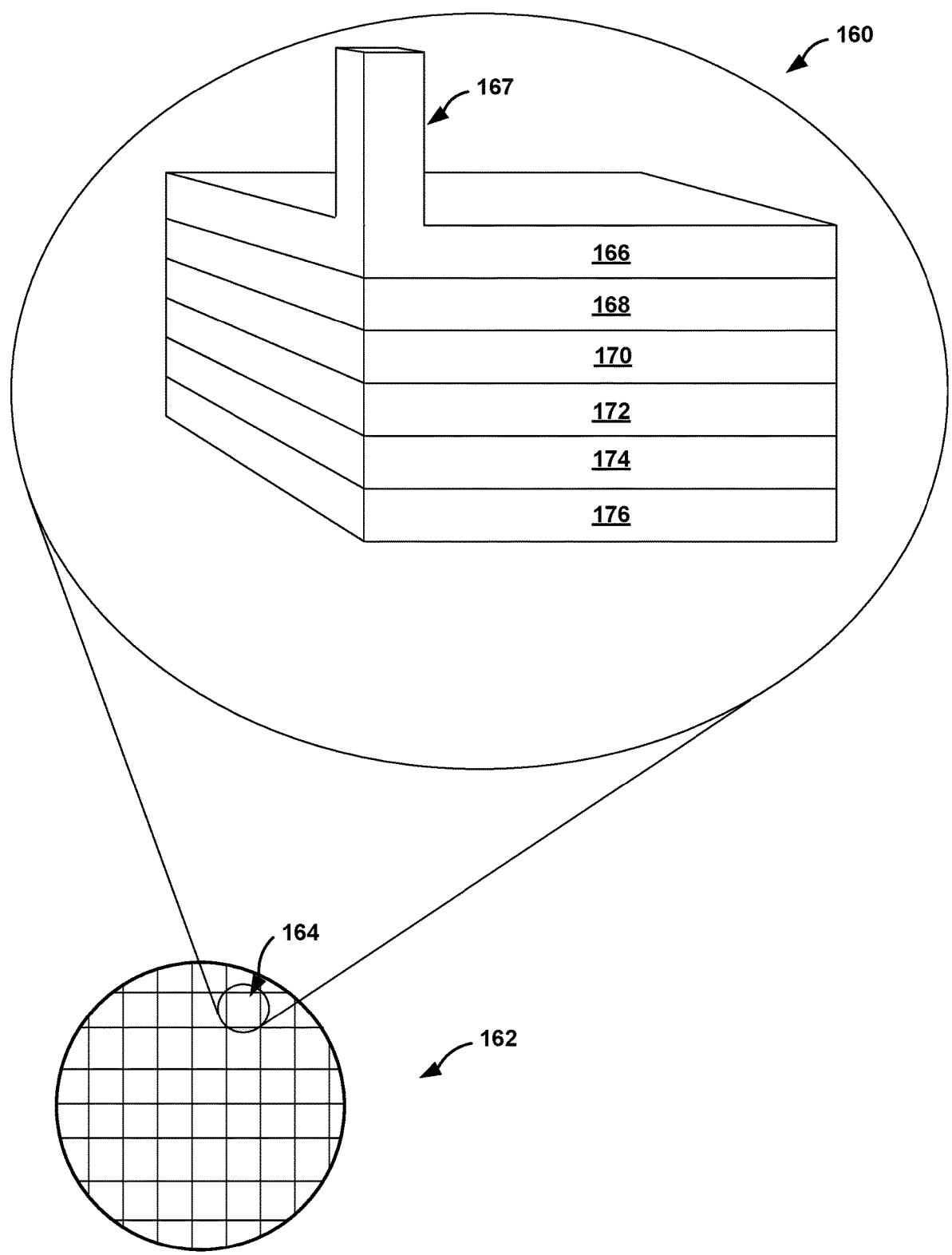
FIG. 6 is a schematic and conceptual diagram illustrating a perspective view of an example medical device including an electrochemical sensor, processing circuitry, an antenna, and a power source.

In some examples, wafer-scale manufacturing techniques, such as semiconductor manufacturing techniques, may be used to form a wafer-scale medical device having a plurality of functional layers that include an electrochemical sensor, processing circuitry, a power source, and an antenna. FIG. 6 is a schematic and conceptual diagram illustrating a perspective view of an example wafer-scale medical device 160 including electrochemical sensor layers 166 and 168, circuitry layers 170 and 172, a power source layer 174, and an antenna layer 176. Wafer-scale medical device 160 may be the same as or substantially similar to medical devices 100 and 130 illustrated in FIGS. 4 and 5, except for the differences describe herein.

In some examples, sensor layer 166 and/or 168 may define protrusion 167 configured to be transcutaneously insertable into a biological system. For example, protrusion 167 may be inserted in the skin of a patient. In some examples, protrusion 167 may include sensor layer 166 and/or 168. In some examples, protrusion 167 may extend between about 2 millimeters and about 20 millimeters, such as 8 millimeters, from a surface wafer-scale device 160. In some examples, wafer-scale device 160 may be fabricated to allow the desired length of protrusion 167 to extend from a surface of wafer-scale device 160. By protrusion 167 extending form a surface of wafer-scale device 160, sensor layers 166 and/or 168 may be fluidly coupled to a biological system, such as the interstitial fluid of a patient.

In some examples, wafer-scale technology may be utilized to build a large number of wafer-scale medical devices from a substrate, such as semiconductor wafer, defining a foundation wafer 162. As one non-limiting example, up to 184 individual wafer-scale medical devices 164 may be fabricated using one ten-inch semiconductor foundation wafer 162. Foundation wafer 162 may include any suitable thickness, such as between about 0.1 millimeters to about 1.1 millimeters. In some examples, the die size for each individual wafer-scale medical devices 164 may be approximately 10.5 millimeters by 10.5 millimeters square. Of course, any suitable diameter and thickness for the substrate can be utilized, and the size of each die location can be selected to accommodate the needs of the particular example. Each respective wafer-scale medical device 164 is realized as a discrete stack of functional layers (e.g., electrochemical sensor layers 166 and 168, circuitry layers 170 and 172, a power source layer 174, and an antenna layer 176), and each stack is coupled to foundation wafer 162. In some examples, a cap or "lid" structure may be fabricated from another substrate, such as another semiconductor wafer. The cap structure may be coupled overlying foundation wafer 162 in a way that creates enclosures for individual wafer-scale medical device 164. Thereafter, the individual wafer-scale medical devices may be cut or otherwise separated into discrete wafer-scale medical devices (e.g., wafer-scale medical device 164).

Electrochemical sensor layers 170 and 172 may be the same as or substantially similar to electrochemical sensor 50 illustrated in FIG. 2. For example, electrochemical sensor layer 170 may include a work platform (e.g., work platform 56) including a plurality of work electrodes (e.g., work electrodes 58). Electrochemical sensor layer 172 may include at least one counter electrode (e.g., counter electrode 52) and a common reference electrode (e.g., common reference electrode 54). In some examples, electrochemical sensor layer 170 may be operatively coupled to electrochemical sensor layer 172 by one or more through vias. In some examples, wafer-scale medical device 160 may include one electrochemical sensor layer, or more electrochemical sensor layers, such as three or four electrochemical sensor layers. Electrochemical sensor layer 170 may be fluidly coupled with an environment surrounding wafer-scale medical device 160 (e.g., a sample fluid). In some examples, electrochemical sensor layer 170 may include one or more apertures to enable electrochemical sensor layer 172 to fluidly coupled with an environment surrounding wafer-scale medical device 160 (e.g., a sample fluid). In this way, electrochemical sensor layers 170 and 172 may be configured to detect the concentration of each of a plurality of analytes present in a sample fluid.

Circuitry layers 170 and 172 may include processing circuitry, communication circuitry, and data storage components operatively coupled to electrochemical sensor layers 166 and 168 to receive from electrochemical sensor layers 166 and 168 a plurality of signals from a plurality of respective work electrodes. In some examples, circuitry layers 170 and 172 may include semiconductor devices, such as integrated chips manufactures and interconnected on a silicon substrate. In some examples, at least a portion of circuitry layer 170 may be formed on at least a portion of electrochemical sensor layer 168. In some examples, at least a portion of circuitry layer 172 may be formed on at least a portion of circuitry layer 170.

Power source layer 174 may include a solid-state battery, a lithium ion battery, a lithium ion micro battery, a fuel cell, or the like. In some examples, power source layer 174 may be formed on at least one of circuitry layer 172.

In some examples, antenna layer 176 may include a substrate and an antenna formed in the substrate. For example, the substrate may include a biocompatible polymer, such as polyamide or polyimide, silica glass, or silicon. At least a portion of the substrate may be metallized to form the antenna.

By stacking each of electrochemical sensor layers 166 and 168, circuitry layers 170 and 172, a power source layer 174, and an antenna layer 176, the size of wafer-scale medical device 160 may be reduced. By forming one or more layers on adjacent layers, manufacturing of wafer-scale medical device 160 may be simplified. By manufacturing wafer-scale medical device 160 using semiconductor manufacturing techniques, a plurality of wafer-scale medical devices 160 may be manufactured simultaneously to reduce manufacturing cost and reduce material waste.

Figure 7A:
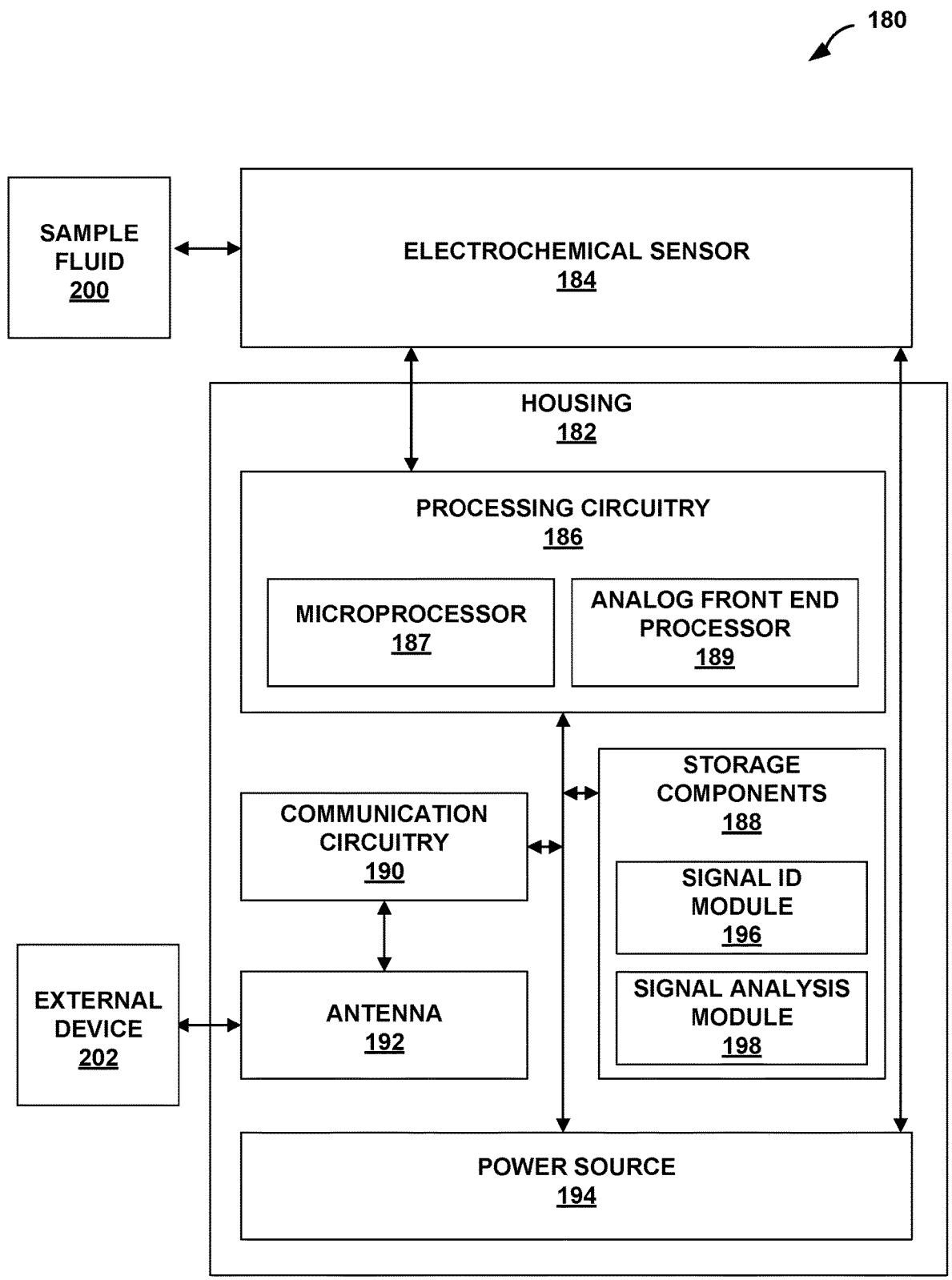
FIG. 7A is a schematic and conceptual block diagram illustrating an example medical device configured to be inserted into the interstitial fluid of a patient.
Figure 7B:
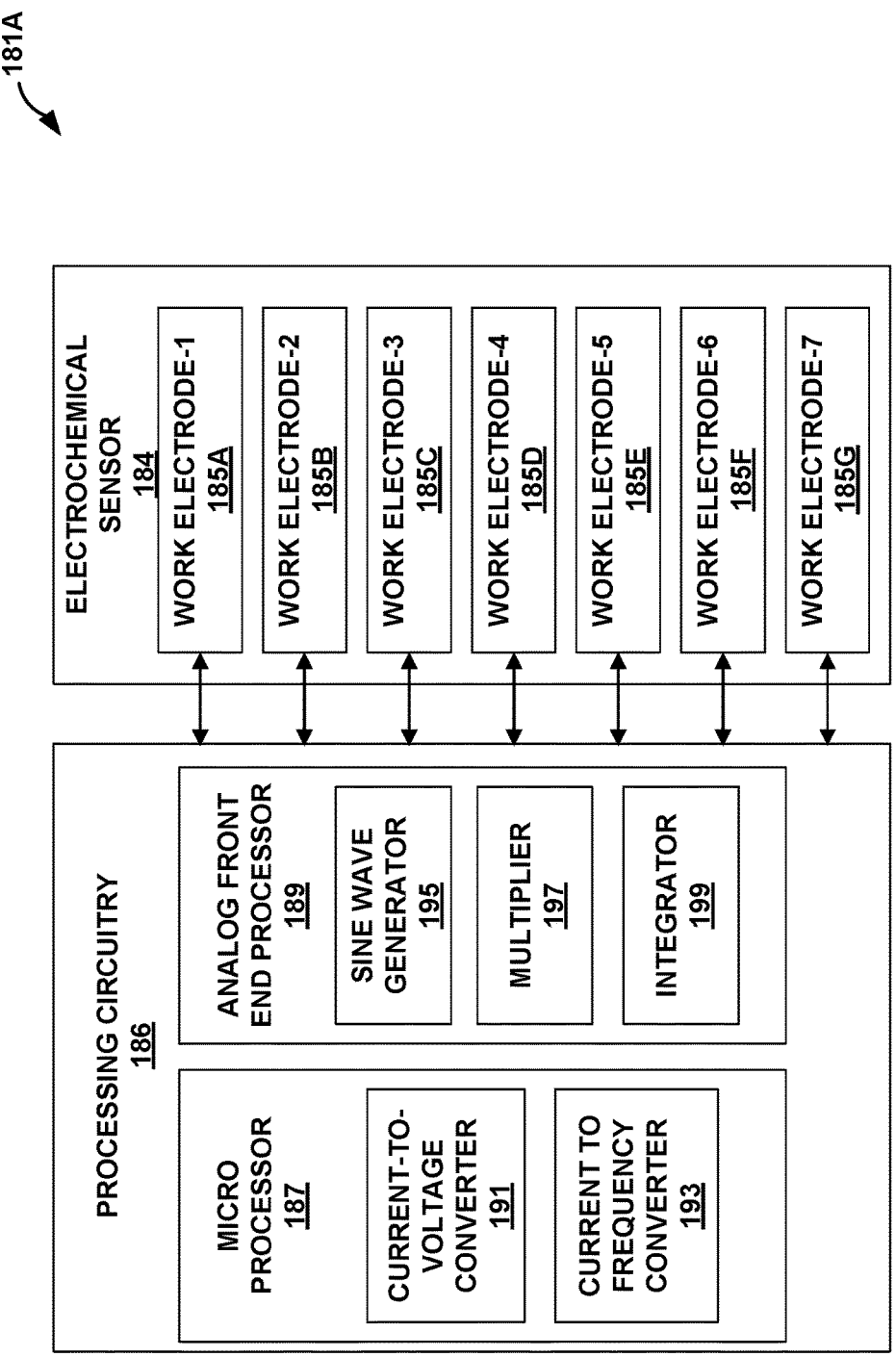
FIGS. 7B-7D are schematic and conceptual block diagrams illustrating example processing circuitry of the example medical device of FIG. 7A.
Figure 7C:
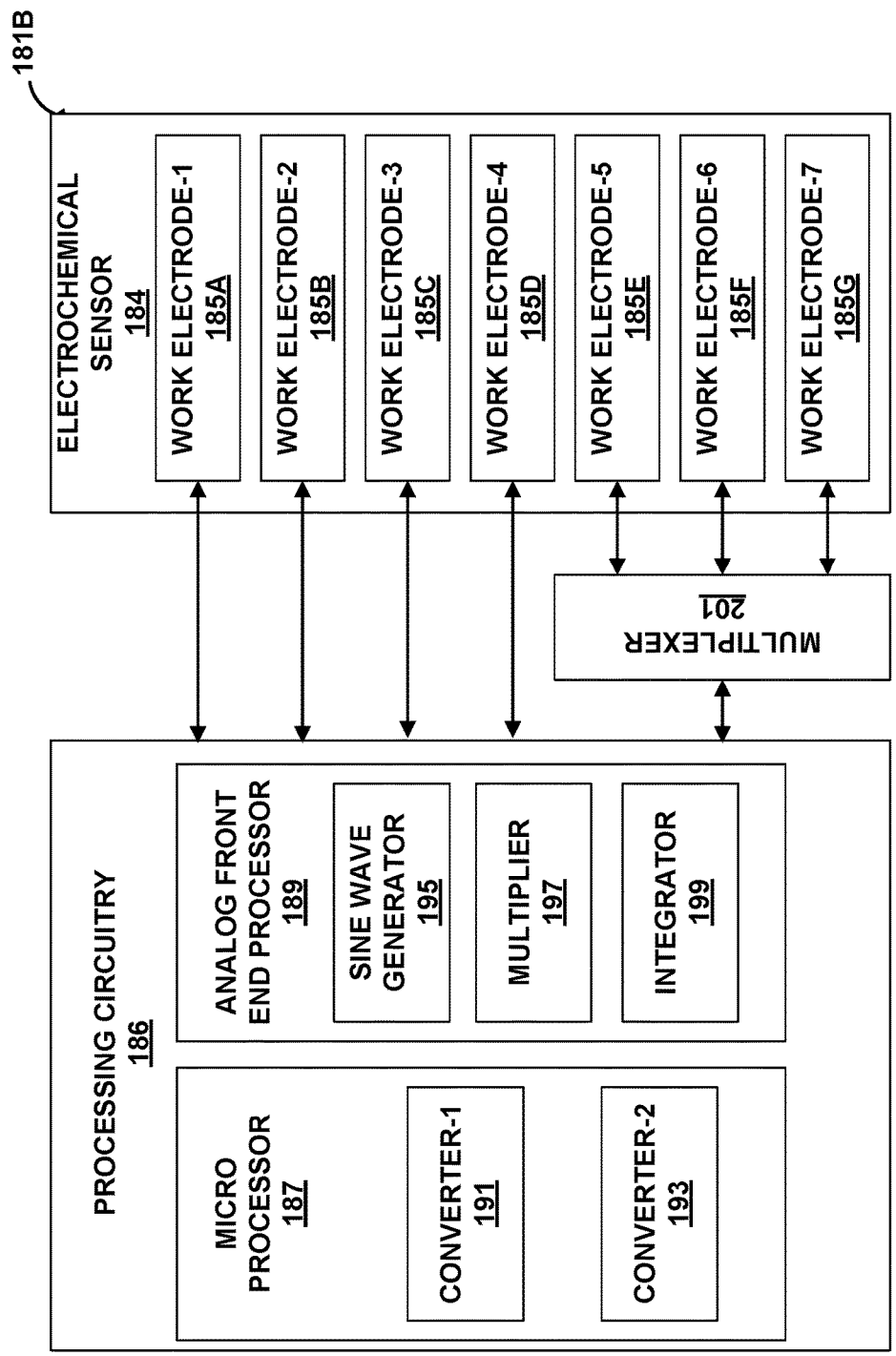
Figure 7D:
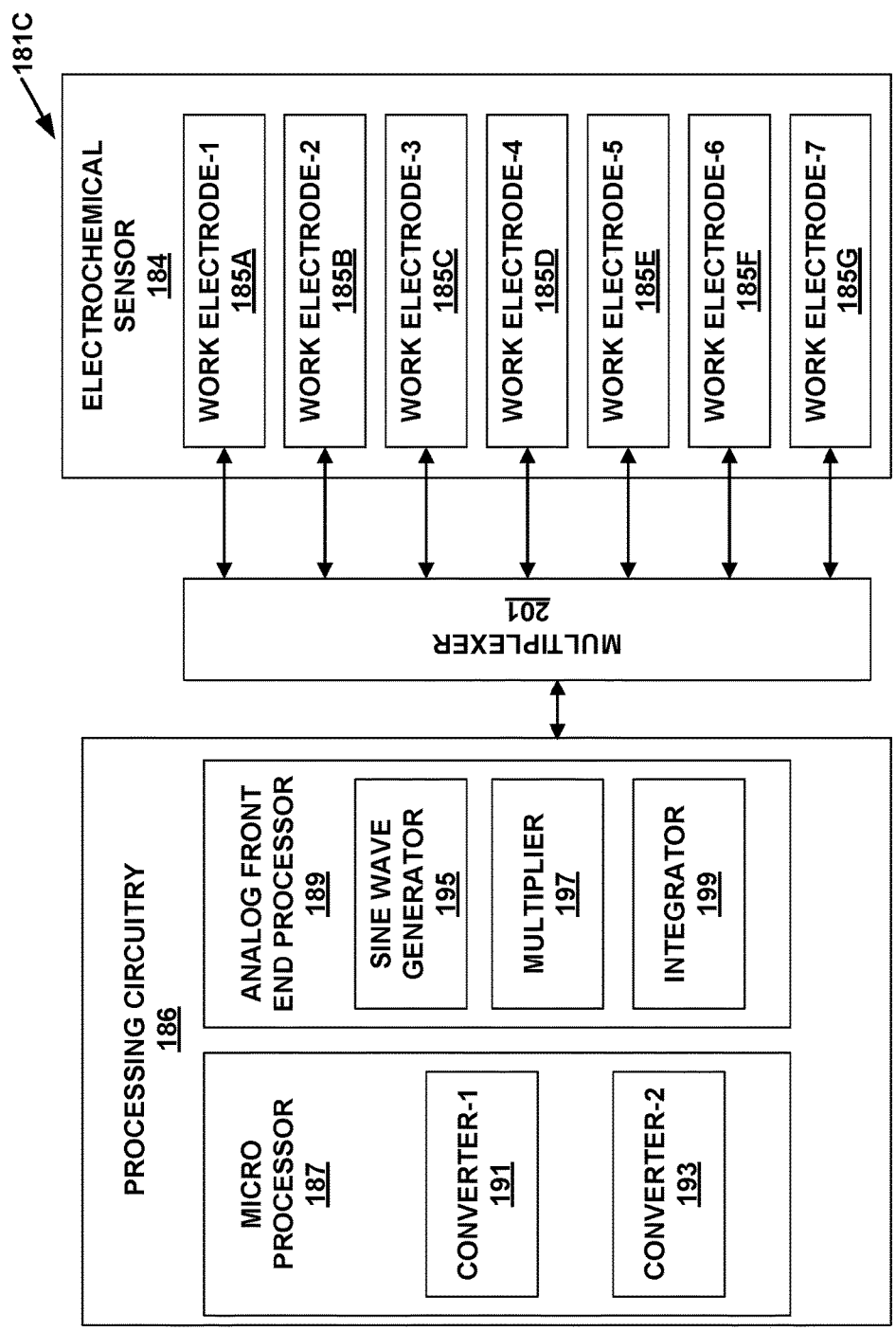

In some examples, an electrochemical sensor may be used in a medical device configured to be inserted within a patient, such as into the interstitial fluid of the patient. FIG. 7A is a schematic and conceptual block diagram illustrating an example medical device 180 configured to be inserted into the interstitial fluid of a patient. Medical device 180 may include a housing 182, an electrochemical sensor 184, processing circuitry 186, storage components 188, communication circuitry 190, an antenna 192, and a power source 194. FIGS. 7B-7D are schematic and conceptual block diagrams illustrating example configurations of medical devices 181A, 181B, and 181C having processing circuitry 186 and electrochemical sensor 184.

In some examples, at least a portion of a dielectric substrate (e.g., dielectric substrate 20) of the components of medical device 180 may define housing 102. For example, in reference to FIG. 6, exterior edges of layers 166, 168, 170, 172, 174, and 176 may define housing 102. In other examples, housing 102 may include a discrete material layer, for example, including but not limited to, a biocompatible coating, biocompatible casing, molded or 3-D printed plastics. Housing 182 may separate at least a portion of the components of medical device 180 including electrochemical sensor 184, processing circuitry 186, storage components 188, communication circuitry 190, an antenna 192, and a power source 194 from the environment surrounding medical device 180, e.g., sample fluid 200. In some examples, one or more components of medical device 180 may be disposed outside housing 182, such as, for example, affixed to an external surface of housing 182. For example, antenna 188 may be affixed to an external surface of housing 182 to improve transmission properties of antenna 192. Housing 182 may include any suitable shape, such as rectilinear or curvilinear. In some examples, housing 182 may be shaped to facilitate insertion of housing 182 into the interstitial fluid of a human patient. For example, housing 182 may include a circular shape to be loaded into an insertion tool or include rounded corners and edges to reduce irritation to the patient.

Housing 180 may be any suitable dimensions. In some examples, a height of housing 102 may be between approximately 1 millimeter and approximately 7 millimeters, such as approximately 2.35 millimeters. In some examples, a width of housing 182 may be between approximately 5 millimeters and approximately 15 millimeters, such as approximately 10.5 millimeters. In some examples, a length of the housing 182 may be between approximately 5 millimeters and approximately 15 millimeters, such as approximately 10.5 millimeters.

In some examples, at least a portion of electrochemical sensor 184 is fluidly coupled to the environment surrounding medical device 180. For example, at least a portion of a work electrode platform of electrochemical sensor 184 may be fluidly coupled to sample fluid 200. In some examples, housing 182 may include one or more apertures exposing at least a portion of electrochemical sensor 184 to sample fluid 200. In examples in which housing 182 includes a coating or a casing, electrochemical sensor 184 may protrude at least partially through a portion of housing 182.

Electrochemical sensor 184 may be the same as or substantially similar to electrochemical sensor 10 illustrated in FIGS. 1A and 1B, electrochemical sensor 50 illustrated in FIG. 2, or electrochemical sensor 80 illustrated in FIG. 3. For example, electrochemical sensor 184 may include a common reference electrode, a counter electrode, and a work electrode platform including a plurality of respective work electrodes 185A, 185B, 185C, 185D, 185E, 185F, and 185G (collectively, "work electrodes 185"). As discussed above, each respective work electrode of work electrodes 185 may be electrically coupled to the common reference electrode and, optionally, at least one counter electrode. Each respective work electrode of work electrodes 185 may include a respective reagent substrate configured to react with a selected analyte to produce a respective signal indicative of a concentration of the selected analyte. In some examples, electrochemical sensor 184 may include a dielectric substrate layer defining a first major surface and interconnect layer on first major surface and defining second major surface, where work electrodes 185 may be disposed on the second major surface and the interconnect layer electrically couples the common reference electrode and the at least one counter electrode to work electrodes 185.

Processing circuitry 186 may include various type of hardware, including, but not limited to, microprocessors, controllers, digital signal processors (DSPs), application specific integrated circuits (ASICs), field-programmable gate arrays (FPGAs), or equivalent discrete or integrated logic circuitry, as well as combinations of such components. The term "processing circuitry" may generally refer to any of the foregoing logic circuitry, alone or in combination with other logic circuitry, or any other equivalent circuitry. In some examples, processing circuitry 186 may represent and/or include additional components, such as sine wave generator 195, multiplier 197, integrators 199, current-to-voltage converter 191, current-to-frequency converter 193, or the like. Processing circuitry 186 represents hardware that can be configured to implement firmware and/or software that sets forth one or more of the algorithms described herein. For example, processing circuitry 186 may be configured to implement functionality, process instructions, or both for execution of processing instructions stored within one or more storage components 188, such as signal identification (ID) module 196 and/or signal analysis module 198.

Processing circuitry 186 is operatively coupled to electrochemical sensor 184 to receive from electrochemical sensor 184 a plurality of signals from work electrodes 185. Processing circuitry 186, e.g., via signal identification module 196, may be configured to identify a respective signal corresponding to a respective selected work electrode of work electrodes 185. For example, processing circuitry 186, e.g., via signal identification module 196, may include multiplexer 201 to identify a respective signal.

Processing circuitry, e.g., via signal analysis module 198, may be configured to process the identified signal to determine the concentration of the respective analyte associated with the respective selected work electrode, as discussed above, by amperometry, potentiometry, and/or EIS. In some examples, processing circuitry 186 may include an analog-to-digital converter communicatively coupled to a microprocessor 187. Microprocessor 187 may be configured to process a respective signal (e.g., converted by the analogto-digital converter) corresponding to a respective selected work electrode of work electrodes 185 to determine the concentration of the respective analyte associated with the respective selected work electrode by amperometry or potentiometry.

In some examples, processing circuitry 186 may include an analog front end (AFE) processor 189 (e.g., an "AFE chip"). AFE processor 189 may be configured to process a respective signal corresponding to a respective selected work electrode of work electrodes 185 to determine the concentration of the respective analyte associated with the respective selected work electrode by amperometry, potentiometry, or EIS. In some examples, as illustrated in FIG. 7B, AFE processor 189 includes a dedicated input for each respective work electrode of work electrodes 185. In some such examples, AFE processor 189 may receive from each respective work electrode of work electrodes 185 a signal including a respective selected frequency for a selected analyte. The respective selected frequency for the selected analyte may be selected to increase a signal response for the selected analyte. For example, a selected frequency for glucose may include about 1000 Hz and a selected frequency for potassium may include about 600 Hz. In other examples, AFE processor 189 may receive a respective signal from each respective work electrode of work electrodes 185 including a respective frequency sweep (e.g., various frequencies ranging from about 1 Hz up to about 100 KHz). The frequency sweep may include at least one frequency or frequency range that results in a response signal from a selected analyte.

In other examples, as illustrated in FIG. 7C, AFE processor 189 may include a dedicated input for each respective work electrode of a first group of work electrodes (e.g., work electrodes 185A-185D in FIG. 7C) from work electrodes 185 and may include an input electrically connected to a multiplexer 201. Multiplexer 201 may be electrically connected to a second group of work electrodes (e.g., work electrodes 185E-185G in FIG. 7C) from work electrodes 185. AFE processor 189 may receive from each of the first group of respective work electrodes of work electrodes 185 (e.g., work electrodes 185A-185D) a respective signal including a respective selected frequency for a selected analyte. AFE processor 189 may receive from multiplexer 201 respective signals from each work electrode of the second group of electrodes 185 (e.g., work electrodes 185E-185G). The respective signals may include a respective selected frequency or a respective frequency sweep for each of the second group of work electrodes 185. In this way, some of work electrodes 185 may be interrogated directly while others may be interrogated in parallel via multiplexer 201.

In other examples, as illustrated in FIG. 7D, AFE processor 189 may be electrically connected to each work electrode of work electrodes 185 via multiplexer 201. AFE processor 189 may receive from multiplexer 201 an identified respective selected frequency for each respective work electrode of work electrodes 185 or an identified respective frequency sweep for each respective work electrode of work electrodes 185. In this way, medical device 180 may identify and process a plurality of signals, each respective signal of the plurality of signals corresponding to a respective work electrode of work electrodes 185.

Medical device 180 may include communications circuitry 190 operatively coupled to processing circuitry 186 and configured to send and receive signals to enable communication with an external device 202 via antenna 192. For example, communications circuitry 190 may include a communications interface, such as a radio frequency transmitter and/or receiver, cellular transmitter and/or receiver, a Bluetooth® interface card, or any other type of device that can send information or send and receive information. In some examples, the communications interface of communications circuitry 190 may be configured to send and/or receive data via antenna 192. In some examples, medical device 180 uses communications circuitry 190 to wirelessly transmit (e.g., a one-way communication) data to external device 202. In some examples, external devices 202 may include, but is not limited to, a radio frequency identification reader, a mobile device, such as a cell phone or tablet, or a computing device operatively coupled to an electronic medical records database or remote server system. In this way, antenna 112 may be operatively coupled to the processing circuitry and configured to transmit data representative of the concentration of the respective analyte to external device 112.

In some examples, processing circuitry 186 may cause communication circuitry 190 to transmit, via antenna 192, data indicative of a determined concentration of an analyte, such as processed data, unprocessed signals from electrochemical sensor 184, or both. In some examples, external device 202 may continuously or periodically interrogate or poll communications circuitry 190 via antenna 192 to cause processing circuitry 186 to receive, identify, or process signals from electrochemical sensor 184. By receiving, identifying, or processing signals from electrochemical sensor 184 only when interrogated or polled by external device 202, processing circuitry may conserve power or processing resources.

One or more storage components 188 may be configured to store information within medical device 180. One or more storage components 188, in some examples, include a computer-readable storage medium or computer-readable storage device. In some examples, one or more storage components 188 include a temporary memory, meaning that a primary purpose of one or more storage components 188 is not long-term storage. One or more storage components 188, in some examples, include a volatile memory, meaning that one or more storage components 188 does not maintain stored contents when power is not provided to one or more storage components 188. Examples of volatile memories include random access memories (RAM), dynamic random-access memories (DRAM), static random-access memories (SRAM), and other forms of volatile memories known in the art. In some examples, one or more storage components 188 are used to store program instructions for execution by processing circuitry 186. One or more storage components 188, in some examples, are used by software or applications running on processing circuitry 186 to temporarily store information during program execution.

In some examples, one or more storage components 188 may further include one or more storage components 188 configured for longer-term storage of information. In some examples, one or more storage components 188 include non-volatile storage elements. Examples of such non-volatile storage elements include flash memories, or forms of electrically programmable memories (EPROM) or electrically erasable and programmable (EEPROM) memories.

As noted above, storage components 188 may store signal identification module 196 and signal analysis module 198. Each of signal identification module 196 and signal analysis module 198 may be implemented in various ways. For example, one or more of signal identification module 196 and signal analysis module 198 may be implemented as an application or a part of an application executed by processing circuitry 186. In some examples, one or more of signal identification module 196 and signal analysis module 198 may be implemented as part of a hardware unit of medical device 180 (e.g., as circuitry). In some examples, one or more of sig signal identification module 196 and signal analysis module 198 may be implemented remotely on external device 202 as part of an application executed by one or more processors of external device 202 or as a hardware unit of external device 202. Functions performed by one or more of signal identification module 196 and signal analysis module 198 are explained below with reference to the example flow diagrams illustrated in FIG. 10.

Power source 194 may be operatively coupled to processing circuitry 186, storage components 188, and/or communication circuitry 190. In some examples, power source 194 may be operatively coupled to electrochemical sensor 184, for example, to supply a working potential or working current to a respective work electrode of the plurality of respective work electrodes. Power source 194 may include any suitable power source, such as, for example, solid state battery, a lithium ion battery, a lithium ion micro battery, a fuel cell, or the like.

Figure 8:
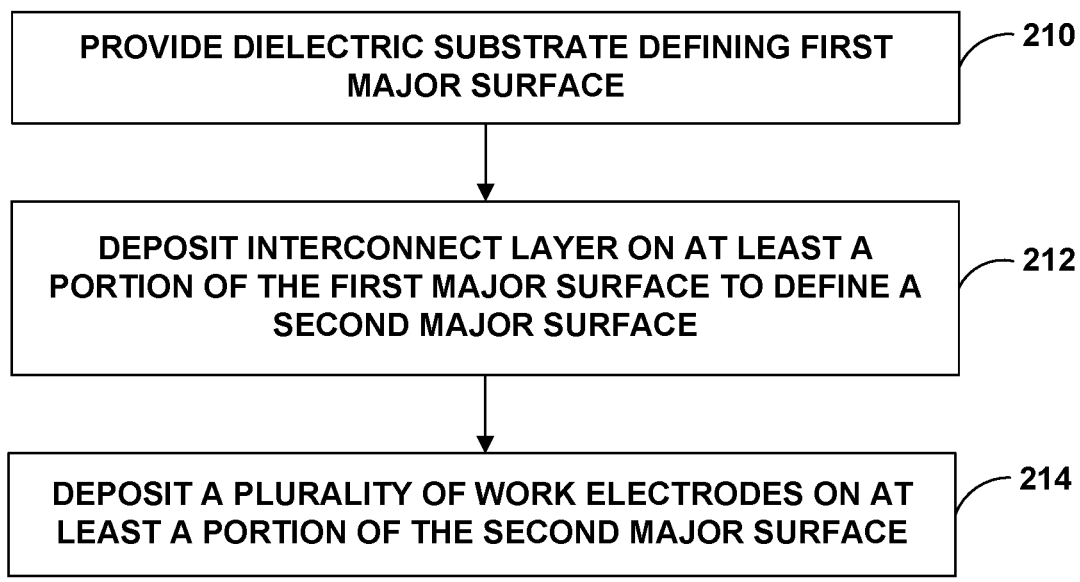
FIG. 8 is a flow diagram illustrating an example technique of forming an electrochemical sensor including a work platform having a plurality of respective work electrodes.

Medical device 180, including electrochemical sensor 184, may be formed using any suitable technique. FIG. 8 is a flow diagram illustrating an example technique of forming an electrochemical sensor. Although the technique illustrated in FIG. 8 will be described with respect to electrochemical sensor 10 of FIGS. 1A and 1B, in some examples, the technique illustrated in FIG. 8 may be used to form other electrochemical sensors, including, but not limited to, electrochemical sensor 50 illustrated in FIG. 2, electrochemical sensor 80 illustrated in FIG. 3, electrochemical sensor 101 illustrated in FIG. 4, electrochemical sensor 131 illustrated in FIG. 5, and electrochemical sensor layers 166 and 168 illustrated in FIG. 6.

The technique illustrated in FIG. 8 includes providing dielectric substrate 20 defining first major surface 24 (210). In some examples, providing dielectric substrate 20 may include forming surface features in dielectric substrate 20, such as, for example, dielectric barriers 98, by, for example, machining, laser etching, or chemical etching. In some examples, providing dielectric substrate 20 may include providing a wafer including a plurality of regions, each region defining dielectric substrate 20. For example, a wafer may include approximately 184 regions. By using a wafer, a plurality of electrochemical sensors 10 may be manufactured substantially simultaneously.

The technique illustrated in FIG. 8 also includes depositing interconnect layer 22 on at least a portion of first major surface 24 to define second major surface 26 opposite first major surface 24 (212). In some examples, depositing interconnect layer 22 may include metallizing first major surface 24 by, for example, chemical vapor deposition, physical vapor deposition, sputtering, thermal spraying, cold spraying, or the like. In some examples, depositing interconnect layer 22 may include polishing at least a portion of second major surface 26 or etching at least a portion of second major surface 26 to define discrete electrical interconnects. Second major surface 26 may provide a suitable surface for subsequent deposition of work electrodes 18, counter electrode 12, and/or common reference electrode 14.

The technique illustrated in FIG. 8 also includes depositing work electrodes 18 on at least a portion of second major surface 26 (214). In some examples, each respective work electrode of work electrodes 18 may include a respective reagent substrate (e.g., reagent substrates 28) configured to react with a respective analyte to produce a signal indicative of a concentration of the respective analyte. By depositing work electrodes 18 on at least a portion of second major surface 26, each respective work electrode of work electrodes 18 may be configured to conduct a signal indicative of a concentration of the respective analyte to interconnect layer 22.

In some examples, depositing the plurality of respective work electrodes may include positioning a mask on at least a portion of second major surface 26 to define an unmasked area of second major surface 26. In some examples, the mask may include any suitable material configured to releasably adhere to second major surface, such as, for example, a photoresist. Depositing the plurality of respective work electrodes may also include depositing a reagent substrate layer (e.g., reagent substrates 28) on the unmasked area. In some examples, depositing the reagent substrate layer may include a preparation of the unmasked area, such as, for example, exposure to a chemical etchant or selected wavelength of radiation. Depositing the plurality of respective work electrodes may also include removing the mask, for example, by a mask stripper. Depositing the plurality of respective work electrodes may also include depositing a membrane layer on at least a portion of the reagent substrate layer. In some examples, the membrane layer may include a limiting membrane or a selective ion transfer membrane, as discussed above. In this way, depositing the plurality of respective work electrodes may include forming a respective work electrode of work electrodes 18 having a reagent substrate and a membrane, as discussed above.

In some examples, depositing the plurality of respective work electrodes may include depositing a second mask on second major surface 26, the reagent substrate layer, and/or the membrane layer to define a second unmasked area. In some examples, the second mask may include any suitable material configured to releasably adhere to second major surface 26, the reagent substrate layer, and/or the membrane layer, such as, for example, a photoresist. Depositing the plurality of respective work electrodes may also include depositing a second membrane layer on the second unmasked area. In some examples, depositing the second membrane layer may include a preparation of the second unmasked area, such as, for example, exposure to a chemical etchant or selected wavelength of radiation. Depositing the plurality of respective work electrodes may also include removing the second mask, for example, by a mask stripper. In some examples, the second membrane layer may include a limiting membrane or a selective ion transfer membrane, as discussed above. In this way, depositing the plurality of respective work electrodes may include forming a respective work electrode of work electrodes 18 having a reagent substrate and a plurality of membranes, as discussed above.

The technique illustrated in FIG. 8 optionally includes depositing common reference electrode 14 on at least a portion of second major surface 26 and depositing counter electrode 12 on at least a portion of second major surface 26. In this way, work electrodes 18 may be operatively coupled to common reference electrode 14 and counter electrode 12.

In some examples, the technique illustrated in FIG. 8 optionally includes stacking work platform 16 on counter electrode 12 and/or common reference electrode 14. For example, the technique optionally includes providing a second dielectric substrate 60B defining third major surface 64B. The technique optionally includes depositing second interconnect layer 62B on at least a portion of third major surface 64B to define fourth major surface 66B opposite third major surface 64B. The technique optionally includes depositing common reference electrode 54 on at least a portion of fourth major surface 64B. The technique optionally includes depositing counter electrode 52 on at least a portion of fourth major surface 64B. The technique optionally includes electrically coupling at least a portion of interconnect layer 22 to at least a portion of second interconnect layer 62B. In this way, work platform 16 may be stacked on counter electrode 12 and/or common reference electrode 14 to reduce the surface area of electrochemical sensor 10.

Figure 9:
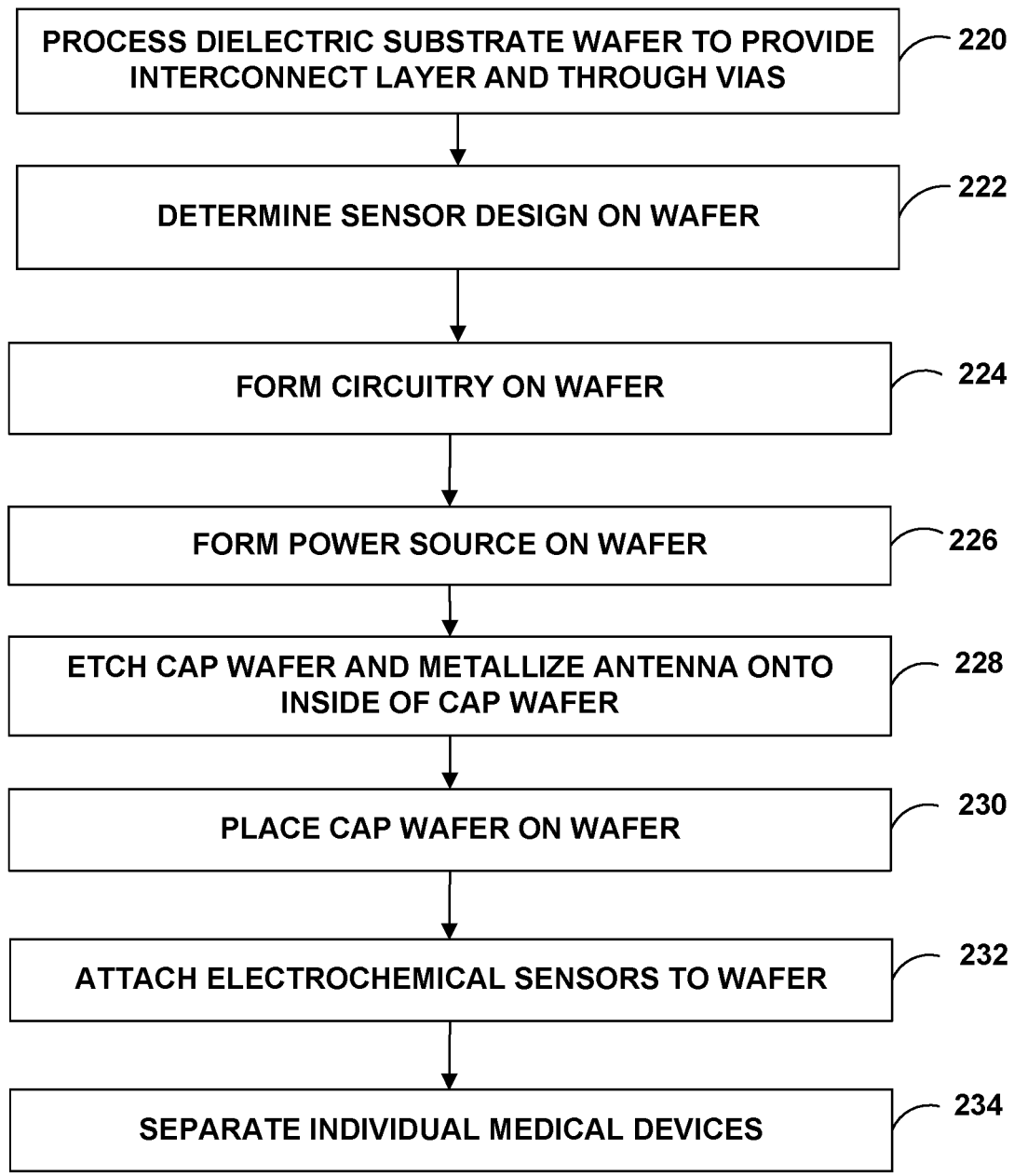
FIG. 9 is a flow diagram illustrating an example technique of forming a medical device including an electrochemical sensor, processing circuitry, an antenna, and a power source.

In some examples, forming an electrochemical sensor, as illustrated in FIG. 8, may be performed as part of a technique of forming a medical device. FIG. 9 is a flow diagram illustrating an example technique of forming a medical device including an electrochemical sensor, processing circuitry, an antenna, and a power source. Although the technique illustrated in FIG. 9 will be described with respect to electrochemical sensor 10 illustrated FIGS. 1A and 1B and medical device 180 illustrated in FIG. 7, in some examples, the technique illustrated in FIG. 9 may be used to form other electrochemical sensors and medical devices, including, but not limited to, electrochemical sensors 50 and 80 illustrated FIGS. 2 and 3 and medical devices 100, 130, and 160 illustrated in FIGS. 4, 5, and 6.

The technique illustrated in FIG. 9 includes processing a wafer (e.g., foundation wafer 162 illustrated in FIG. 6) including dielectric substrate 20 to provide interconnect layer 22 on first major surface 24 of dielectric substrate 20 and through vias 68 (220). In some examples, processing wafer 162 may include metallizing first major surface 24 by, for example, chemical vapor deposition, physical vapor deposition, thermal spraying, cold spraying, dip coating, spin coating, jetting deposition, or the like. In some examples, depositing interconnect layer 22 may include polishing at least a portion of second major surface 26 or etching at least a portion of second major surface 26. In some examples, processing wafer 162 to include through vias (e.g., a via-first-, via-middle-, or via-last-through-silicon via, through-glass via, or through-chip via) may include mechanical etching or chemical etching. By processing wafer 162 to provide interconnect layer 22 and through vias 68, wafer 162 may be prepared to receive one or more components of electrochemical sensor 10 or circuitry, such a processing circuitry 106.

The technique illustrated in FIG. 9 also includes, after processing wafer 162 to provide interconnect layer 22 and through vias 68, determining a sensor design on wafer 162 (222). In some examples, a sensor design may be overlaid on wafer 162 to enable processing equipment to determine boundaries of respective die locations corresponding to each respective medical devices (e.g., medical devices 180 illustrated in FIG. 6) of a plurality of medical devices to be manufactured on a single wafer 162. In some examples, determining sensor design may include defining physical and/or electrical features of each electrochemical sensor. For example, defining physical and/or electrical features of each electrochemical sensor forming a base polyimide layer, metallizing, forming an intermediate polyimide layer, etching, and/or forming a top polyimide layer. In some examples, the chemistry related steps associated with formation of the electrochemical sensors may be performed during subsequent steps. In this way, a plurality of electrochemical sensor patterns may be defined and formed directly on the surface of wafer 162 by conventional techniques and methodologies for creating physiological sensor elements of the type described here.

The technique illustrated in FIG. 9 also includes forming circuitry on wafer 162 (224). In some examples, forming circuitry on wafer 162 may include forming a conductive circuit pattern overlaying a surface of wafer 162 opposite the surface of wafer 162 including the sensor design in step 222. In some examples, forming circuitry may include positioning a plurality of integrated chips on wafer 162, such as, for example, a silicon-based wafer including a plurality of integrated chips corresponding to each die location on wafer 162. In some examples, a plurality of consecutive layers of a plurality of integrated chips may be positioned on wafer 162. For example, each consecutive layer of the plurality of consecutive layers may include one or more of processing circuitry 186, storage components 188, and communicant circuitry 190. The circuitry includes individual circuit layouts (which are the same or substantially similar) for each respective die location (i.e., each respective medical device 180 of a plurality of medical devices on wafer 162). The circuitry for each die location includes electrically conductive traces, contact pads, and features designed for compatibility with the multilayer component stack to be mounted to the die location.

The technique illustrated in FIG. 9 also includes forming power source 194 on wafer 162 (226). In some examples, forming power source 194 on wafer 162 may include operatively coupling power source 194 to the circuitry, such as processing circuitry 186, storage components 188, or communicant circuitry 190. In some examples, forming power source 194 on wafer 162 may include positioning a plurality of power sources on wafer 162, the plurality of power sources corresponding to the arrangement of medical devices 180 on wafer 162. In some examples, forming power source 194 on wafer 162 may include forming a plurality of power sources on wafer 162, the plurality of power sources corresponding to the arrangement of medical devices 180 on wafer 162.

The technique illustrated in FIG. 9 also includes etching a cap wafer and metallizing antenna 192 onto inside of the cap wafer (228). In some examples, a cap wafer may include a second wafer configured to be placed over wafer 162, e.g., after placing power source 192 on wafer 162. In some examples, the cap wafer includes the same material as foundation wafer 162. In other examples, the cap wafer includes a polymer or plastic material. In some examples, etching the cap wafer may include mechanical etching or chemical etching to define a cavity. In some examples, the cavities can be etched or otherwise formed in an arrangement that is designed and configured to individually enclose each of the multilayer component stacks. In some examples, at least a portion of the cavity may correspond to a selected shape of antenna 192. In some examples, metallizing antenna 192 onto inside of the cap wafer may include disposition of a metal by, for example, chemical vapor deposition, physical vapor deposition, thermal spraying, cold spraying, or the like, into the cavity formed in the cap wafer. In some examples, metallizing antenna 192 onto inside of cap wafer may include placing one or more electrical couplings configured to electrically couple antenna 192 to the circuitry, such as to communications circuitry 190. In some examples, the cap wafer may include a plurality of antennas 192, each antenna of the plurality of antennas corresponding to a medical device 180 on wafer 162.

The technique illustrated in FIG. 9 also includes placing cap wafer on wafer 162 (230). The cap wafer can be attached overlying the surface of the foundation wafer 162 to "seal" each respective medical device 180 of the plurality of medical devices. The seal may be hermetic or non-hermetic. In examples in which the seal is hermetic, medical device 180 may have improved performance, improved device longevity, or both. In some examples, the cap wafer may be attached to the foundation wafer 162 using epoxy, a wafer bond material, or the like. In some examples, placing cap wafer on wafer 162 may include placing cap wafer on power source 194. In this way, the cap wafer may be configured to encapsulate power source 194. For example, when inserted into a sample fluid 200, power source 194 may be isolate from sample fluid 200. In some examples, the cap wafer may be configured to dissipate heat produced at power source 194, e.g., cap wafer may include one or more baffles configured to improve heat transfer from power source 194 to an environment surrounding medical device 180, such as sample fluid 200. By placing the cap wafer on power source 194, medical device 180 may reduce exposure of a patient to power source 194.

The technique illustrated in FIG. 9 also includes forming electrochemical sensor 10 on wafer 162 (232). In some examples, forming electrochemical sensor 10 on wafer 162 may include placing electrochemical sensor 10 on side of wafer 162 opposing the circuitry, power source 194, or antenna 192. In some examples, forming electrochemical sensor 10 may include forming electrochemical sensor 10 using the technique illustrated in FIG. 8. In some examples, forming electrochemical sensor 10 using the technique illustrated in FIG. 8 may include forming a plurality of respective electrochemical sensors 10 of respective medical devices 180 of a plurality of medical devices on wafer 162.

The technique illustrated in FIG. 9 also includes separating individual medical devices 180 of the plurality of medical devices on wafer 162 (234). In some examples, separating individual medical devices 180 may include mechanically separating individual medical devices 180 by, for example, laser cutting, laser etching, chemical etching, or machining material between each adjacent medical device 180 of the plurality of medical devices. In this way, the technique illustrated in FIG. 9 may be used to form a plurality of medical devices 180.

Figure 10:
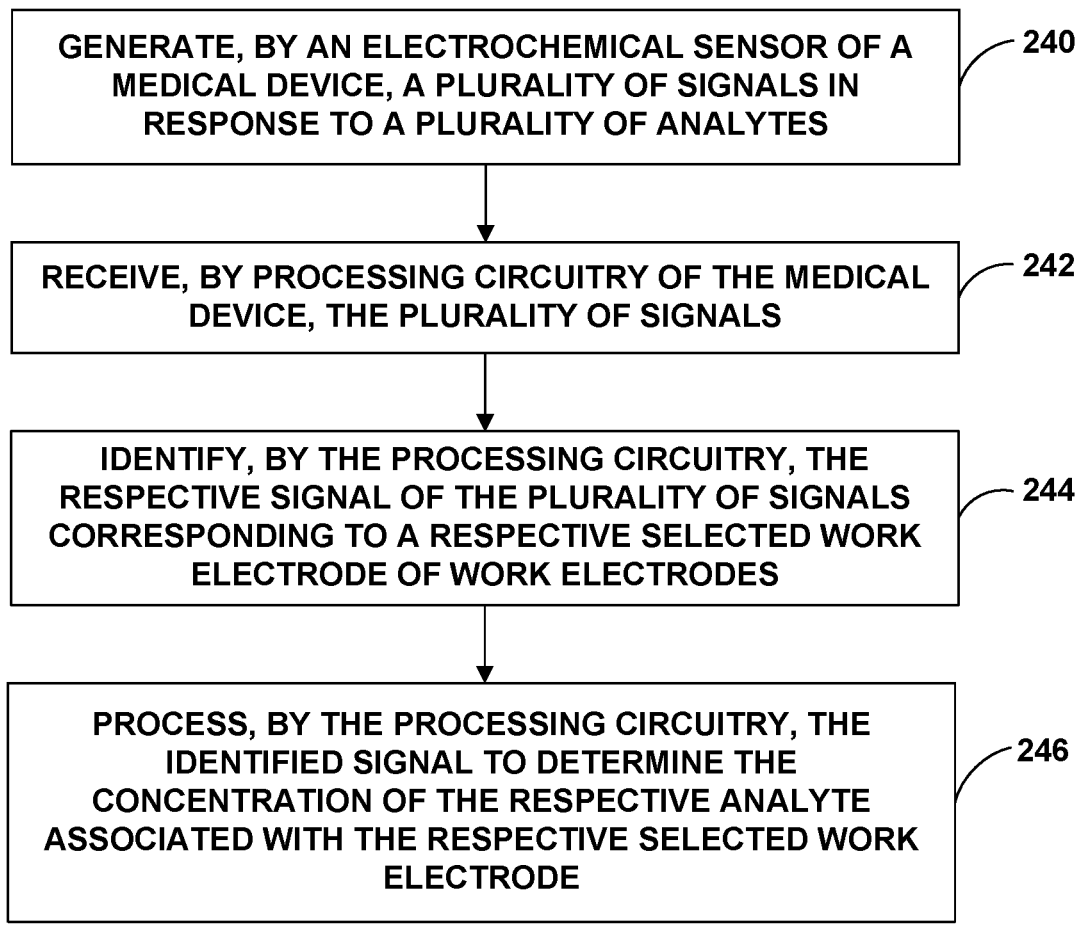
FIG. 10 is a flow diagram illustrating an example technique of detecting concentration of an analyte.

A medical device including an electrochemical sensor formed by the techniques illustrated in FIG. 9 may be used detect the concentration of an analyte in a sample fluid. FIG. 10 is a flow diagram illustrating an example technique of detecting concentration of an analyte. Although the technique illustrated in FIG. 10 will be described with respect to medical device 100 illustrated in FIG. 4 including electrochemical sensor 10 of FIGS. 1A and 1B, in some examples, the technique illustrated in FIG. 10 may use other medical devices or other electrochemical sensors to detect a concentration of an analyte, including, but not limited to, electrochemical sensors 50 or 80 illustrated in FIGS. 2 and 3, and medical devices 100, 130, 160, and 180 illustrated in FIGS. 4, 5, 6, and 7.

The technique illustrated in FIG. 10 includes generating, by electrochemical sensor 104 of medical device 100, a plurality of signals in response to a plurality of analytes (240). For example, electrochemical sensor 104 may be the substantially similar to electrochemical sensor 10 described with respect to FIGS. 1A and 1B. As discussed above, each respective work electrode of work electrode 18 may generate a signal (e.g., a current and/or a potential) in response to a respective analyte, or derivative thereof, reacting with a respective reagent substrate of the respective work electrode of work electrodes 18.

The technique illustrated in FIG. 10 also includes receiving, by processing circuitry 160 of medical device 100 operatively coupled to electrochemical sensor 104, the plurality of signals (242). In some examples, the plurality of signals may include conditioned signals, unconditioned signals, or both. For example, a portion of the signals may include analogue signals and a portion of the signals may include digital signals.

The technique illustrated in FIG. 10 also includes identifying, by processing circuitry 106, e.g., signal identification module 116, the respective signal of the plurality of signals corresponding to a respective selected work electrode of work electrodes 18 (244). In some examples, identifying the respective signal of the plurality of signals may include using timing signals to associate the respective signal with a selected work electrode of work electrodes 18. In some examples, identifying the respective signal of the plurality of signals may include using a multiplexer to associate the respective signal with a selected work electrode of work electrodes 18. By identifying the respective signal associated with a selected work electrode of work electrodes 18, processing circuitry 106, e.g., signal identification module 116, may determine an appropriate technique to process the respective signal.

The technique illustrated in FIG. 10 also includes processing, by processing circuitry 106, e.g., signal analysis module 118, the identified signal to determine the concentration of the respective analyte associated with the respective selected work electrode (246). For example, processing circuitry 106 may process the identified signal by at least one of amperometry, potentiometry, or EIS. In some examples, the identified signal may include a current, such as change in current between the respective work electrode of work electrode 18 and common reference electrode 14, such that processing circuity may determine a concentration of the respective analyte based at least in part on amperometry, as discussed above. In some examples, the identified signal may include a potential, such as a difference in the potential between the respective work electrode of work electrode 18 and common reference electrode 14, such that processing circuity 106 may determine a concentration of the respective analyte based at least in part on potentiometry, as discussed above. In some examples, the identified signal may include a response signal, such as a current between the respective work electrode of work electrode 18 and counter electrode 12 in response to an excitation signal, such that processing circuitry 106, e.g., signal analysis module 118, may determine a concentration of the respective analyte base at least in part on EIS, as discussed above.

In some examples, the technique illustrated in FIG. 10 may be performed while medical device 100 is disposed within a biological system, such as inserted within an interstitial fluid of a human patient.

In some examples, the technique illustrated in FIG. 10 optionally includes transmitting, by antenna 112 operatively coupled to processing circuitry 106, the determined concentration of the respective analyte to external device 122. In some examples, external device 122 may be located outside of the biological system, such as outside of the interstitial fluid of a human patient.

The following clauses include example subject matter of the present disclosure.

Clause 1. An electrochemical sensor comprising a common reference electrode; at least one counter electrode; and a work electrode platform comprising a plurality of respective work electrodes, wherein each respective work electrode of the plurality of respective work electrodes is electrically coupled to the common reference electrode and comprises a respective reagent substrate configured to react with a respective analyte to produce a signal indicative of a concentration of the respective analyte.

Clause 2. The electrochemical sensor of Clause 1, comprising a dielectric substrate defining a first major surface; and an interconnect layer on the first major surface and defining a second major surface opposing the first major surface, wherein the plurality of respective work electrodes are disposed on the second major surface, and wherein the interconnect layer electrically couples the common reference electrode and the at least one counter electrode to the plurality of respective work electrodes.

Clause 3. The electrochemical sensor of Clause 1 or 2, wherein at least one respective work electrode of the plurality of respective work electrodes comprises a membrane disposed on the respective reagent substrate, and wherein the membrane is permeable to the respective analyte.

Clause 4. The electrochemical sensor of Clause 3, wherein the membrane comprises a limiting membrane, a selective ion transfer membrane, or a limiting membrane and a selective ion transfer membrane.

Clause 5. The electrochemical sensor of Clause 3 or 4, wherein the membrane comprises an ionophore.

Clause 6. The electrochemical sensor of any one of Clauses 1 to 5, wherein the at least one respective work electrode comprises a limiting membrane on the respective reagent substrate and a selective ion transfer membrane on the limiting membrane.

Clause 7. The electrochemical sensor of any one of Clauses 1 to 5, wherein the at least one respective work electrode comprises a selective ion transfer membrane on the respective reagent substrate and a limiting membrane on the selective ion transfer membrane.

Clause 8. The electrochemical sensor of any one of Clauses 3 to 7, wherein the membrane includes at least one ionophore selected from the group consisting of: amino methylated polystyrene salicylaldehyde, dibenzo-18-crown-6, cezomycin, enniatin, gramicidin A, lasalocid, macrolides, monensin, narasin, nigericin, nigericin sodium salt, nonactin, polyimide/lycra blend, salinomycin, valinomycin, or mixtures thereof.

Clause 9. The electrochemical sensor of any one of Clauses 1 to 8, wherein each respective work electrode of the plurality of respective work electrodes comprises a respective membrane disposed on the respective reagent substrate, and wherein the respective membrane is selectively permeable to the respective analyte.

Clause 10. The electrochemical sensor of any one of Clauses 1 to 9, wherein at least one of the respective reagent substrates comprises an oxidase enzyme.

Clause 11. The electrochemical sensor of any one of Clauses 1 to 10, wherein the respective reagent substrate includes at least one enzyme selected from the group consisting of: glucose oxidase, creatinine amidohydrolase, creatine amidohydrolase, sarcosine oxidase, carbonic anhydrase, choline oxidase, horseradish peroxidase, thiamine oxidase, urease, glycerol-3-phosphate oxidase, L-amino acid oxidase, lactate oxidase, catalase alkaline phosphatase, alcohol oxidase, D-amino acid oxidase, cholesterol oxidase, pyridoxal oxidase, and NAD(P)H oxidase, and pyruvate oxidase, or mixtures thereof.

Clause 12. The electrochemical sensor of any one of Clauses 1 to 11, wherein the respective reagent substrate includes a respective immobilization substrate configured to immobilize a respective reagent.

Clause 13. The electrochemical sensor of any one of Clauses 1 to 12, wherein a length of each respective work electrode of the plurality of respective work electrodes is between about 0.25 millimeters and about 0.75 millimeters, and wherein a width of each respective work electrode of the plurality of respective work electrodes is between about 0.25 millimeters and about 0.75 millimeters.

Clause 14. The electrochemical sensor of any one of Clauses 1 to 13, wherein a length of the at least one counter electrode is between about 7.5 millimeters and about 10 millimeters, and wherein a width of the at least one counter electrode is between about 7.5 millimeters and about 10 millimeters.

Clause 15. The electrochemical sensor of any one of Clauses 1 to 14, wherein the work electrode platform comprises a dielectric barrier disposed between a first work electrode of the plurality of respective work electrodes and a second work electrode of the plurality of respective work electrodes adjacent to the first work electrode.

Clause 16. The electrochemical sensor of any one of Clauses 1 to 15, wherein the interconnect layer comprises at least one electrical interconnect comprising chromium, a gold chromium alloy, titanium, a titanium gold alloy, or platinum.

Clause 17. The electrochemical sensor of any one of Clauses 1 to 16, wherein the plurality of respective work electrodes comprises: a first work electrode comprising a first reagent substrate configured to react with sodium ions; a second work electrode comprising a second reagent substrate configured to react with chloride ions; a third work electrode comprising a third reagent substrate configured to react with blood urea nitrogen; a fourth work electrode comprising a fourth reagent substrate configured to react with glucose; a fifth work electrode comprising a fifth reagent substrate configured to react with potassium; a sixth work electrode comprising a sixth reagent substrate configured to react with bicarbonate or carbon dioxide; and a seventh work electrode comprising a seventh reagent substrate configured to react with creatinine.

Clause 18. The electrochemical sensor of any one of Clauses 1 to 17, wherein the plurality of respective work electrodes is electrically coupled in common to the common reference electrode and the at least one counter electrode.

Clause 19. The electrochemical sensor of any one of Clauses 2 to 18, wherein the plurality of respective work electrodes is electrically connected to a single, common electrical interconnect in the interconnect layer.

Clause 20. The electrochemical sensor of any one of Clauses 1 to 19, comprising a single common reference electrode and a single counter electrode.

Clause 21. A biocompatible medical device comprising: an electrochemical sensor comprising: a common reference electrode; at least one counter electrode; and a work electrode platform comprising a plurality of respective work electrodes, wherein each respective work electrode of the plurality of respective work electrodes is electrically coupled to the common reference electrode and comprises a respective reagent substrate configured to react with a respective analyte to produce a respective signal indicative of a concentration of the respective analyte; processing circuitry operatively coupled to the electrochemical sensor, wherein the processing circuitry is configured to: receive from the electrochemical sensor a plurality of signals from the plurality of respective work electrodes; identify the respective signal corresponding to a respective selected work electrode of the plurality of respective work electrodes; and process the identified signal to determine the concentration of the respective analyte associated with the respective selected work electrode; an antenna operatively coupled to the processing circuitry; and a power source operatively coupled to the processing circuitry.

Clause 22. The biocompatible medical device of Clause 21, wherein at least a portion of the work electrode platform is fluidly coupled to an environment surrounding the biocompatible medical device.

Clause 23. The biocompatible medical device of Clause 21 or 22, wherein a height of the biocompatible medical device is approximately 2.35 millimeters, wherein a width of the biocompatible medical device is approximately 10.5 millimeters, and wherein a length of the biocompatible medical device is approximately 10.5 millimeters.

Clause 24. The biocompatible medical device of any one of Clauses 21 to 23, wherein the antenna is configured to transmit data representative of the concentration of the respective analyte to an external device.

Clause 25. The biocompatible medical device of any one of Clauses 21 to 24, wherein the electrochemical sensor comprises: a dielectric substrate defining a first major surface; and an interconnect layer on the first major surface and defining a second major surface opposing the first major surface, wherein the plurality of respective work electrodes are disposed on the second major surface, and wherein the interconnect layer electrically couples the common reference electrode and the at least one counter electrode to the plurality of respective work electrodes.

Clause 26. The biocompatible medical device of any one of Clauses 21 to 25, wherein at least one work electrode of the plurality of respective work electrodes comprises a membrane disposed on the respective reagent substrate, and wherein the respective membrane is permeable to the respective analyte.

Clause 27. The biocompatible medical device of Clause 26, wherein the membrane comprises a limiting membrane, a selective ion transfer membrane, or a limiting membrane and a selective ion transfer membrane.

Clause 28. The biocompatible medical device of Clause 26 or 27, wherein the membrane comprises an ionophore.

Clause 29. The biocompatible medical device of any one of Clauses 21 to 28, wherein the at least respective work electrode comprises a limiting membrane on the respective reagent substrate and a selective ion transfer membrane on the limiting membrane.

Clause 30. The biocompatible medical device of any one of Clauses 21 to 28, wherein the at least respective work electrode comprises a selective ion transfer membrane on the respective reagent substrate and a limiting membrane on the selective ion transfer membrane.

Clause 31. The biocompatible medical device of any one of Clauses 26 to 30, wherein the membrane includes at least one ionophore selected from the group consisting of: amino methylated polystyrene salicylaldehyde, dibenzo-18-crown-6, cezomycin, enniatin, gramicidin A, lasalocid, macrolides, monensin, narasin, nigericin, nigericin sodium salt, nonactin, polyimide/lycra blend, salinomycin, valinomycin, or mixtures thereof.

Clause 32. The biocompatible medical device of any one of Clauses 21 to 31, wherein each respective work electrode of the plurality of respective work electrodes comprises a respective membrane disposed on the respective reagent substrate, and wherein the respective membrane is selectively permeable to the respective analyte.

Clause 33. The biocompatible medical device of any one of Clauses 21 to 32, wherein at least one of the respective reagent substrates comprises an oxidase enzyme.

Clause 34. The biocompatible medical device of any one of Clauses 21 to 33, wherein the respective reagent substrate includes at least one enzyme selected from the group consisting of: glucose oxidase, creatinine amidohydrolase, creatine amidinohydrolase, sarcosine oxidase, carbonic anhydrase, choline oxidase, horseradish peroxidase, thiamine oxidase, urease, glycerol-3-phosphate oxidase, L-amino acid oxidase, lactate oxidase, catalase alkaline phosphatase, alcohol oxidase, D-amino acid oxidase, cholesterol oxidase, pyridoxal oxidase, and NAD(P)H oxidase, and pyruvate oxidase, or mixtures thereof.

Clause 35. The biocompatible medical device of any one of Clauses 21 to 34, wherein a length of each respective work electrode of the plurality of respective work electrodes is between about 0.25 millimeters and about 0.75 millimeters, and wherein a width of each respective work electrode of the plurality of respective work electrodes is between about 0.25 millimeters and about 0.75 millimeters.

Clause 36. The biocompatible medical device of any one of Clauses 21 to 35, wherein a length of the at least one counter electrode is between about 7.5 millimeters and about 10 millimeters, and wherein a width of the at least one counter electrode is between about 7.5 millimeters and about 10 millimeters.

Clause 37. The biocompatible medical device of any one of Clauses 21 to 36, wherein the work electrode platform comprises a dielectric barrier disposed between a first work electrode of the plurality of respective work electrodes and a second work electrode of the plurality of respective work electrodes adjacent to the first work electrode.

Clause 38. The biocompatible medical device of any one of Clauses 25 to 37, wherein the interconnect layer comprises at least one electrical interconnect comprising chromium, a gold chromium alloy, titanium, a titanium gold alloy, or platinum.

Clause 39. The biocompatible medical device of any one of Clauses 21 to 38, wherein the plurality of respective work electrodes comprises: a first work electrode comprising a first reagent substrate configured to react with sodium ions; a second work electrode comprising a second reagent substrate configured to react with chloride ions; a third work electrode comprising a third reagent substrate configured to react with blood urea nitrogen; a fourth work electrode comprising a fourth reagent substrate configured to react with glucose; a fifth work electrode comprising a fifth reagent substrate configured to react with potassium; a sixth work electrode comprising a sixth reagent substrate configured to react with bicarbonate or carbon dioxide; and a seventh work electrode comprising a seventh reagent substrate configured to react with creatinine.

Clause 40. The biocompatible medical device of any one of Clauses 21 to 39, wherein the plurality of respective work electrodes is electrically coupled in common to the common reference electrode and the at least one counter electrode.

Clause 41. The biocompatible medical device of any one of Clauses 25 to 40, wherein the plurality of respective work electrodes is electrically connected to a single, common electrical interconnect in the interconnect layer.

Clause 42. The biocompatible medical device of any one of Clauses 21 to 41, comprising a single common reference electrode and a single counter electrode.

Clause 43. A method of forming an electrochemical sensor, the method comprising: forming a common reference electrode; forming at least one counter electrode; and forming a work electrode platform comprising a plurality of respective work electrodes on at least a portion of the second major surface, wherein each respective work electrode of the plurality of respective work electrodes comprises a respective reagent substrate configured to react with a respective analyte to produce a signal indicative of a concentration of the respective analyte.

Clause 44. The method of Clause 43, comprising: providing a dielectric substrate defining a first major surface; forming an interconnect layer on the first major surface to define a second major surface opposite the first major surface, wherein forming the work electrode platform comprises forming the plurality of respective work electrodes on the second major surface, and wherein the interconnect layer electrically couples the common reference electrode and the at least one counter electrode to the plurality of respective work electrodes.

Clause 45. The method of Clause 43 or 44, wherein at least one of the respective reagent substrates comprises an oxidase enzyme.

Clause 46. The method of any one of Clauses 43 to 45, wherein the respective reagent substrate includes at least one enzyme selected from the group consisting of: glucose oxidase, creatinine amidohydrolase, creatine amidinohydrolase, sarcosine oxidase, carbonic anhydrase, choline oxidase, horseradish peroxidase, thiamine oxidase, urease, glycerol-3-phosphate oxidase, L-amino acid oxidase, lactate oxidase, catalase alkaline phosphatase, alcohol oxidase, D-amino acid oxidase, cholesterol oxidase, pyridoxal oxidase, and NAD(P)H oxidase, and pyruvate oxidase, or mixtures thereof.

Clause 47. The method of any one of Clauses 43 to 46, wherein a length of each respective work electrode of the plurality of respective work electrodes is between about 0.25 millimeters and about 0.75 millimeters, and wherein a width of each respective work electrode of the plurality of respective work electrodes is between about 0.25 millimeters and about 0.75 millimeters.

Clause 48. The method of any one of Clauses 44 to 47, wherein the interconnect layer comprises at least one electrical interconnect comprising chromium, a gold chromium alloy, titanium, a titanium gold alloy, or platinum.

Clause 49. The method of any one of Clauses 44 to 48, comprising: depositing a common reference electrode on at least a portion of the second major surface; and depositing at least one counter electrode on at least a portion of the second major surface.

Clause 50. The method of any one of Clauses 44 to 49, comprising: providing a second dielectric substrate defining a third major surface; depositing a second interconnect layer on at least a portion of the third major surface to form a second interconnect layer defining a fourth major surface opposite the third major surface; and depositing a common reference electrode on at least a portion of the fourth major surface; depositing at least one counter electrode on at least a portion of the fourth major surface; and electrically coupling at least a portion of the interconnect layer to at least a portion of the second interconnect layer.

Clause 51. The method of any one of Clauses 43 to 50, wherein a length of the at least one counter electrode is between about 7.5 millimeters and about 10 millimeters, and wherein a width of the at least one counter electrode is between about 7.5 millimeters and about 10 millimeters.

Clause 52. The method of any one of Clauses 43 to 51, wherein depositing the plurality of respective work electrodes comprises: positioning a mask on at least a portion of the second major surface to define an unmasked area of the second major surface; depositing a reagent substrate layer on the unmasked area; removing the mask; and depositing a membrane layer on at least a portion of the reagent substrate layer.

Clause 53. The method of Clause 52, wherein depositing the plurality of respective work respective electrodes comprises: depositing a second mask on the membrane layer to define a second unmasked area; depositing a second membrane on the second unmasked area; and removing the second mask.

Clause 54. The method of Clause 52 or 53, wherein the membrane layer or the second membrane layer comprises a limiting membrane, a selective ion transfer membrane, or a limiting membrane and a selective ion transfer membrane.

Clause 55. The method of any one of Clauses 52 to 54, wherein the membrane layer or the second membrane layer comprises an ionophore.

Clause 56. The method of any one of Clauses 52 to 55, wherein the membrane layer comprises a limiting membrane on the reagent substrate layer, and wherein the second membrane layer comprises a selective ion transfer membrane on the limiting membrane.

Clause 57. The method of any one of Clauses 52 to 56, wherein the membrane layer comprises a selective ion transfer membrane on the reagent substrate layer, and wherein the second membrane layer comprises a limiting membrane on the selective ion transfer membrane.

Clause 58. The method of any one of Clauses 52 to 57, wherein the membrane layer or the second membrane layer includes at least one ionophore selected from the group consisting of: amino methylated polystyrene salicylaldehyde, dibenzo-18-crown-6, cezomycin, enniatin, gramicidin A, lasalocid, macrolides, monensin, narasin, nigericin, nigericin sodium salt, nonactin, polyimide/lycra blend, salinomycin, valinomycin, or mixtures thereof.

Clause 59. The method of any one of Clauses 43 to 58, wherein depositing the plurality of respective work electrodes comprises depositing a dielectric barrier between a first work electrode of the plurality of respective work electrodes and a second work electrode of the plurality of respective work electrodes adjacent to the first work electrode.

Clause 60. A method of detecting a concentration of an analyte, the method comprising generating, by an electrochemical sensor of a medical device, a plurality of signals in response to a plurality of analytes, wherein the electrochemical sensor comprises a common reference electrode; at least one counter electrode; and a work electrode platform comprising a plurality of respective work electrodes, wherein each respective work electrode of the plurality of respective work electrodes is electrically coupled to the common reference electrode and comprises a respective reagent substrate configured to react with a respective analyte to produce a respective signal of the plurality of signals indicative of a concentration of the respective analyte; and receiving, by processing circuitry of the medical device operatively coupled to the electrochemical sensor, the plurality of signals; identifying, by the processing circuitry, the respective signal of the plurality of signals corresponding to a respective selected work electrode of the plurality of respective work electrodes; and processing, by the processing circuitry, the identified signal to determine the concentration of the respective analyte associated with the respective selected work electrode.

Clause 61. The method of Clause 60, wherein the medical device is disposed within a biological system.

Clause 62. The method of Clause 60 or 61, wherein the medical device is inserted within an interstitial fluid of a human patient.

Clause 63. The method of any one of Clauses 60 to 62, comprising transmitting, by an antenna operatively coupled to the processing circuitry, the determined concentration of the respective analyte to an external device located outside of the biological system or interstitial fluid.

Clause 64. The method of any one of Clause 60 to 63, wherein the electrochemical sensor comprises:
a dielectric substrate defining a first major surface; and
an interconnect layer on the first major surface and defining a second major surface opposing the first major surface, wherein the plurality of respective work electrodes are disposed on the second major surface, and wherein the interconnect layer electrically couples the common reference electrode and the at least one counter electrode to the plurality of respective work electrodes.

Clause 65. The method of any one of Clause 60 to 64, wherein at least one work electrode of the plurality of respective work electrodes comprises a membrane disposed on the respective reagent substrate, and wherein the respective membrane is permeable to the respective analyte.

Clause 66. The method of Clause 65, wherein the membrane comprises a limiting membrane, a selective ion transfer membrane, or a limiting membrane and a selective ion transfer membrane.

Clause 67. The method of Clause 65 or 66, wherein the membrane comprises an ionophore.

Clause 68. The method of any one of Clauses 60 to 67, wherein the at least respective work electrode comprises a limiting membrane on the respective reagent substrate and a selective ion transfer membrane on the limiting membrane.

Clause 69. The method of any one of Clauses 60 to 68, wherein the at least respective work electrode comprises a selective ion transfer membrane on the respective reagent substrate and a limiting membrane on the selective ion transfer membrane.

Clause 70. The method of any one of Clauses 65 to 69, wherein the membrane includes at least one ionophore selected from the group consisting of: amino methylated polystyrene salicylaldehyde, dibenzo-18-crown-6, cezomycin, enniatin, gramicidin A, lasalocid, macrolides, monensin, narasin, nigericin, nigericin sodium salt, nonactin, polyimide/lycra blend, salinomycin, valinomycin, or mixtures thereof.

Clause 71. The method of any one of Clauses 60 to 70, wherein each respective work electrode of the plurality of respective work electrodes comprises a respective membrane disposed on the respective reagent substrate, and wherein the respective membrane is selectively permeable to the respective analyte.

Clause 72. The method of any one of Clauses 60 to 71, wherein the respective reagent substrate comprises an oxidase enzyme.

Clause 73. The method of any one of Clauses 60 to 72, wherein the respective reagent substrate includes at least one enzyme selected from the group consisting of: glucose oxidase, creatinine amidohydrolase, creatine amidinohydrolase, sarcosine oxidase, carbonic anhydrase, choline oxidase, horseradish peroxidase, thiamine oxidase, urease, glycerol-3-phosphate oxidase, L-amino acid oxidase, lactate oxidase, catalase alkaline phosphatase, alcohol oxidase, D-amino acid oxidase, cholesterol oxidase, pyridoxal oxidase, and NAD(P)H oxidase, and pyruvate oxidase, or mixtures thereof.

Clause 74. The method of any one of Clauses 60 to 73, wherein a length of each respective work electrode of the plurality of respective work electrodes is between about 0.25 millimeters and about 0.75 millimeters, and wherein a width of each respective work electrode of the plurality of respective work electrodes is between about 0.25 millimeters and about 0.75 millimeters.

Clause 75. The method of any one of Clauses 60 to 74, wherein a length of the at least one counter electrode is between about 7.5 millimeters and about 10 millimeters, and wherein a width of the at least one counter electrode is between about 7.5 millimeters and about 10 millimeters.

Clause 76. The method of any one of Clauses 60 to 75, wherein the work electrode platform comprises a dielectric barrier disposed between a first work electrode of the plurality of respective work electrodes and a second work electrode of the plurality of respective work electrodes adjacent to the first work electrode.

Clause 77. The method of any one of Clauses 60 to 76, wherein the interconnect layer comprises at least one electrical interconnect comprising chromium, a gold chromium alloy, titanium, a titanium gold alloy, or platinum.

Various examples have been described. These and other examples are within the scope of the following claims.

What is claimed is:

1. An electrochemical sensor comprising:
a dielectric substrate defining a first major surface;
an interconnect layer on the first major surface and defining a second major surface opposing the first major surface, and
a common reference electrode;
at least one counter electrode; and
a work electrode platform comprising a plurality of respective work electrodes,
wherein the plurality of respective work electrodes are disposed on the second major surface,
wherein the interconnect layer electrically couples the common reference electrode and the at least one counter electrode to each respective work electrode of the plurality of respective work electrodes, and
wherein each respective work electrode of the plurality of respective work electrodes comprises a respective reagent substrate configured to react with a respective analyte to produce a signal indicative of a concentration of the respective analyte.

2. The electrochemical sensor of claim 1, wherein at least one respective work electrode of the plurality of respective work electrodes comprises a membrane disposed on the respective reagent substrate, and wherein the membrane is permeable to the respective analyte.

3. The electrochemical sensor of claim 2, wherein the membrane comprises a limiting membrane, a selective ion transfer membrane, or a limiting membrane and a selective ion transfer membrane.

4. The electrochemical sensor of claim 2, wherein the membrane comprises an ionophore.

5. The electrochemical sensor of claim 2, wherein the membrane includes at least one ionophore selected from the group consisting of: amino methylated polystyrene salicylaldehyde, dibenzo-18-crown-6, cezomycin, enniatin, gramicidin A, lasalocid, macrolides, monensin, narasin, nigericin, nigericin sodium salt, nonactin, polyimide/lycra blend, salinomycin, valinomycin, or mixtures thereof.

6. The electrochemical sensor of claim 1, wherein the at least one respective work electrode comprises a limiting membrane on the respective reagent substrate and a selective ion transfer membrane on the limiting membrane.

7. The electrochemical sensor of claim 1, wherein the at least one respective work electrode comprises a selective ion transfer membrane on the respective reagent substrate and a limiting membrane on the selective ion transfer membrane.

8. The electrochemical sensor of claim 1, wherein each respective work electrode of the plurality of respective work electrodes comprises a respective membrane disposed on the respective reagent substrate, and wherein the respective membrane is selectively permeable to the respective analyte.

9. The electrochemical sensor of claim 1, wherein at least one of the respective reagent substrates comprises an oxidase enzyme.

10. The electrochemical sensor of claim 1, wherein the respective reagent substrate includes at least one enzyme selected from the group consisting of: glucose oxidase, creatinine amidohydrolase, creatine amidinohydrolase, sarcosine oxidase, carbonic anhydrase, choline oxidase, horseradish peroxidase, thiamine oxidase, urease, glycerol-3-phosphate oxidase, L-amino acid oxidase, lactate oxidase, catalase alkaline phosphatase, alcohol oxidase, D-amino acid oxidase, cholesterol oxidase, pyridoxal oxidase, and NAD(P)H oxidase, and pyruvate oxidase, or mixtures thereof.

11. The electrochemical sensor of claim 1, wherein the respective reagent substrate includes a respective immobilization substrate configured to immobilize a respective reagent.

12. The electrochemical sensor of claim 1, wherein a length of each respective work electrode of the plurality of respective work electrodes is between about 0.25 millimeters and about 0.75 millimeters, and wherein a width of each respective work electrode of the plurality of respective work electrodes is between about 0.25 millimeters and about 0.75 millimeters.

13. The electrochemical sensor of claim 1, wherein a length of the at least one counter electrode is between about 7.5 millimeters and about 10 millimeters, and wherein a width of the at least one counter electrode is between about 7.5 millimeters and about 10 millimeters.

14. The electrochemical sensor of claim 1, wherein the work electrode platform comprises a dielectric barrier disposed between a first work electrode of the plurality of respective work electrodes and a second work electrode of the plurality of respective work electrodes adjacent to the first work electrode.

15. The electrochemical sensor of claim 1, wherein the interconnect layer comprises at least one electrical interconnect comprising chromium, a gold chromium alloy, titanium, a titanium gold alloy, or platinum.

16. The electrochemical sensor of claim 1, wherein the plurality of respective work electrodes comprises:
a first work electrode comprising a first reagent substrate configured to react with sodium ions;
a second work electrode comprising a second reagent substrate configured to react with chloride ions;
a third work electrode comprising a third reagent substrate configured to react with blood urea nitrogen;
a fourth work electrode comprising a fourth reagent substrate configured to react with glucose;
a fifth work electrode comprising a fifth reagent substrate configured to react with potassium;
a sixth work electrode comprising a sixth reagent substrate configured to react with bicarbonate or carbon dioxide; and
a seventh work electrode comprising a seventh reagent substrate configured to react with creatinine.

17. The electrochemical sensor of claim 1, wherein the plurality of respective work electrodes is electrically coupled in common to the common reference electrode and the at least one counter electrode.

18. The electrochemical sensor of claim 1, wherein the plurality of respective work electrodes is electrically connected to a single, common electrical interconnect in the interconnect layer.

19. The electrochemical sensor of claim 1, comprising a single common reference electrode and a single counter electrode.

20. A method of forming an electrochemical sensor, the method comprising:
providing a dielectric substrate defining a first major surface;
forming an interconnect layer on the first major surface to define a second major surface opposite the first major surface;
forming a common reference electrode;
forming at least one counter electrode; and
forming a work electrode platform comprising a plurality of respective work electrodes on at least a portion of the second major surface,
wherein the interconnect layer electrically couples the common reference electrode and the at least one counter electrode to each respective work electrode of the plurality of respective work electrodes, and
wherein each respective work electrode of the plurality of respective work electrodes comprises a respective reagent substrate configured to react with a respective analyte to produce a signal indicative of a concentration of the respective analyte.

21. The method of claim 20, wherein at least one of the respective reagent substrates comprises an oxidase enzyme.

22. The method of claim 20, wherein the respective reagent substrate includes at least one enzyme selected from the group consisting of: glucose oxidase, creatinine amidohydrolase, creatine amidinohydrolase, sarcosine oxidase, carbonic anhydrase, choline oxidase, horseradish peroxidase, thiamine oxidase, urease, glycerol-3-phosphate oxidase, L-amino acid oxidase, lactate oxidase, catalase alkaline phosphatase, alcohol oxidase, D-amino acid oxidase, cholesterol oxidase, pyridoxal oxidase, and NAD(P)H oxidase, and pyruvate oxidase, or mixtures thereof.

23. The method of claim 20, wherein a length of each respective work electrode of the plurality of respective work electrodes is between about 0.25 millimeters and about 0.75 millimeters, and wherein a width of each respective work electrode of the plurality of respective work electrodes is between about 0.25 millimeters and about 0.75 millimeters.

24. The method of claim 20, wherein the interconnect layer comprises at least one electrical interconnect comprising chromium, a gold chromium alloy, titanium, a titanium gold alloy, or platinum.

25. The method of claim 20, comprising:
depositing a common reference electrode on at least a portion of the second major surface; and
depositing at least one counter electrode on at least a portion of the second major surface.

26. The method of claim 20, comprising:
providing a second dielectric substrate defining a third major surface;
depositing a second interconnect layer on at least a portion of the third major surface to form a second interconnect layer defining a fourth major surface opposite the third major surface; and
depositing a common reference electrode on at least a portion of the fourth major surface;
depositing at least one counter electrode on at least a portion of the fourth major surface; and
electrically coupling at least a portion of the interconnect layer to at least a portion of the second interconnect layer.

27. The method of claim 20, wherein a length of the at least one counter electrode is between about 7.5 millimeters and about 10 millimeters, and wherein a width of the at least one counter electrode is between about 7.5 millimeters and about 10 millimeters.

28. The method of claim 20, wherein depositing the plurality of respective work electrodes comprises:
   positioning a mask on at least a portion of the second major surface to define an unmasked area of the second major surface;
   depositing a reagent substrate layer on the unmasked area;
   removing the mask; and
   depositing a membrane layer on at least a portion of the reagent substrate layer.

29. The method of claim 28, wherein depositing the plurality of respective work respective electrodes comprises:
   depositing a second mask on the membrane layer to define a second unmasked area;
   depositing a second membrane on the second unmasked area; and
   removing the second mask.

30. The method of claim 28, wherein the membrane layer or the second membrane layer comprises a limiting membrane, a selective ion transfer membrane, or a limiting membrane and a selective ion transfer membrane.

31. The method of claim 28, wherein the membrane layer or the second membrane layer comprises an ionophore.

32. The method of claim 28, wherein the membrane layer comprises a limiting membrane on the reagent substrate layer, and wherein the second membrane layer comprises a selective ion transfer membrane on the limiting membrane.

33. The method of claim 28, wherein the membrane layer comprises a selective ion transfer membrane on the reagent substrate layer, and wherein the second membrane layer comprises a limiting membrane on the selective ion transfer membrane.

34. The method of claim 28, wherein the membrane layer or the second membrane layer includes at least one ionophore selected from the group consisting of: amino methylated polystyrene salicylaldehyde, dibenzo-18-crown-6, cezomycin, enniatin, gramicidin A, lasalocid, macrolides, monensin, narasin, nigericin, nigericin sodium salt, nonactin, polyimide/lycra blend, salinomycin, valinomycin, or mixtures thereof.

35. The method of claim 20, wherein depositing the plurality of respective work electrodes comprises depositing a dielectric barrier between a first work electrode of the plurality of respective work electrodes and a second work electrode of the plurality of respective work electrodes adjacent to the first work electrode.

* * * * *